United States Patent [19]

Jones et al.

[11] Patent Number: 5,077,309

[45] Date of Patent: Dec. 31, 1991

[54] PROSTAGLANDINS

[75] Inventors: Robert L. Jones; Norman H. Wilson, both of Edinburgh, Scotland

[73] Assignee: National Research Development Corporation, London, United Kingdom

[21] Appl. No.: 501,358

[22] Filed: Mar. 28, 1990

[30] Foreign Application Priority Data

Jan. 16, 1986 [GB] United Kingdom ................ 8600997
Jan. 16, 1986 [GB] United Kingdom ................ 8601018

[51] Int. Cl.$^5$ .................. C07C 177/00; A61K 31/557
[52] U.S. Cl. ................................. 514/469; 514/529; 514/530; 514/542; 514/562; 514/564; 514/565; 546/290; 546/304; 546/310; 548/161; 548/170; 548/180; 548/217; 548/221; 548/222; 549/463; 560/16; 560/34; 560/43; 560/32; 560/118; 560/120; 560/121; 560/125; 560/126; 562/426; 562/439; 562/452; 562/460; 562/500; 562/502; 562/503; 562/507; 562/508

[58] Field of Search ............... 514/469, 529, 530, 542, 514/562, 564, 565; 546/290, 304, 310; 548/161, 170, 180, 217, 221, 222; 549/463, 16, 34; 560/43, 52, 118, 120, 121, 125, 126; 562/426, 439, 452, 460, 500, 502, 503, 507, 508

[56] References Cited

U.S. PATENT DOCUMENTS

| | | | |
|---|---|---|---|
| 4,368,332 | 1/1983 | Jones | 560/120 |
| 4,430,345 | 2/1984 | Jones et al. | 560/12 |
| 4,438,136 | 3/1984 | Jones | 560/120 |
| 4,458,091 | 7/1984 | Jones et al. | 560/12 |
| 4,513,103 | 4/1985 | Das et al. | 560/12 |
| 4,596,823 | 6/1986 | Jones et al. | 560/12 |
| 4,628,061 | 12/1986 | Jones et al. | 560/12 |
| 4,902,717 | 2/1990 | Senior | 514/562 |

FOREIGN PATENT DOCUMENTS

| | | |
|---|---|---|
| 0043292 | 1/1982 | European Pat. Off. . |
| 0044711 | 1/1982 | European Pat. Off. . |
| 082646 | 6/1983 | European Pat. Off. . |
| WO86/04234 | 7/1986 | PCT Int'l Appl. . |
| 2169803 | 7/1986 | United Kingdom . |

OTHER PUBLICATIONS

W. Krause et al., "Biotransformation of the Stable Prostacyclin ... ", Drug Metabolism & Disposition, vol. 12, No. 5, 1984, pp. 645–651.

W. Skuballa et al., "Synthesis of a New Chemically and Metabolical Stable ... ", Jour. of Medicinal Chem., vol. 29, No. 3, Mar. 1986, pp. 313–316.

G. Bundy et al., "Novel Prostaglandin Syntheses", New York Academy of Sciences, pp. 77–90.

Primary Examiner—Robert Gerstl
Attorney, Agent, or Firm—Nixon & Vanderhye

[57] ABSTRACT

Novel compounds have the formula (I)

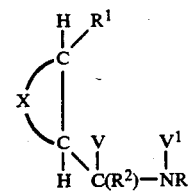

where

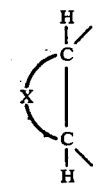

represents one of the divalent cyclic groups

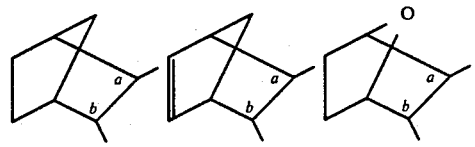

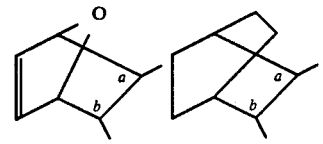

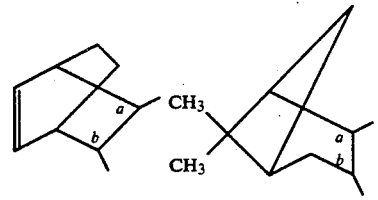

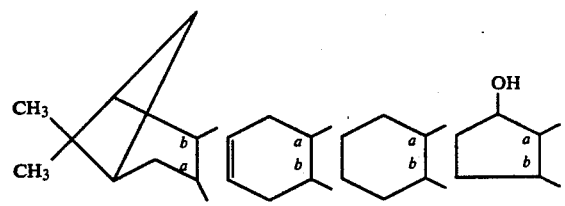

the letters a and b indicating in each case the points of attachment of the substituents $R^1$ and $CV(R^2)$-NV'R, respectively; $R^1$ is a group —$(CH_2)_b$—$(A)_a$—$(CH_2)_c$—B—$CH_2$—$CO_2R'$ in which A and B are each separately oxygen or sulphur, a is 0, b is 0 and c is an integer from 3 to 10, or a is 1, b is 0 or an integer from 1 to 7 and c is an integer from 2 to 9 with the sum of b and c being from 2 to 9, and $CO_2R'$ is a carboxy group or an amide, ester or salt derivative thereof; V and V' either each (Abstract continued on next page.)

separately is hydrogen or together are the second bond of a carbon-nitrogen double bond; $R^2$ is hydrogen, an aliphatic hydrocarbon group or an aliphatic hydrocarbon group substituted by an aromatic group directly or through an oxygen or sulphur atom; and R is a group $-OR^3$, $-OR^4$, $-D-R^3$, $-N=R^5$ or $-NW.G.W'$ in which D is $-NH$, $-NH.CS-$, $-NH.CO-$, $-NH.CO.CH_2N(R^6)-$, $-NH.SO_2-$, $-NH.CO.NH-$, $-NH.CS.NH-$, $-NH.CO.O-$ or $-NH.CS.O-$, G is $-CO-$ or $-CS-$ and W and W' together are a group $-(CH_2)_d-$ in which d is 3, 4, or 5, $R^3$ is an aliphatic hydrocarbon group, an aromatic group or an aliphatic hydrocarbon group substituted by one or more aromatic groups directly or through an oxygen or sulphur atom, $R^4$ is an aliphatic hydrocarbon group which is substituted through an oxygen atom by an aliphatic hydrocarbon group which is itself substituted directly by one or more aromatic groups, $R^5$ is an aliphatic hydrocarbon group, and aromatic group in which the $\pi$-electron system is not fully delocalized over the entire ring system, or aliphatic hydrocarbon group substituted by one or more aromatic groups directly or through an oxygen or sulphur atom, and $R^6$ is hydrogen, an aliphatic hydrocarbon group, an aromatic group or an aliphatic hydrocarbon group substituted by one or more aromatic groups directly or through an oxygen or sulphur atom. The compounds are of value for use in pharmaceutical compositions particularly in the context of the inhibition of thromboxane activity.

37 Claims, No Drawings

PROSTAGLANDINS

This is a continuation of application Ser. No. 07/003,690, filed Jan. 16, 1987, now abandoned.

This invention relates to biologically active compounds and in particular to certain novel compounds exhibiting activity at thromboxane receptor sites.

Thromboxane $A_2$ (TXA$_2$), which is derived from arachidonic acid via prostaglandin $H_2$ (PGH$_2$), is implicated in several potentially noxious actions on various body systems, including platelet aggregation, bronchoconstriction and pulmonary and systemic vasoconstriction. Thus TXA$_2$ may be involved in the normal sealing of blood vessels following injury but in addition may contribute to pathological intravascular clotting or thrombosis. Moreover, the constrictor actions of TXA$_2$ on bronchiolar, pulmonary vascular and systemic vascular smooth muscle may be important in the development of several anaphylactic conditions including bronchial asthma. There is also some evidence to implicate PGH$_2$ and TXA$_2$ in the genesis of inflammation.

Consequently there is a considerable interest in the use as pharmaceuticals of compounds having activity at thromboxane receptor sites, especially compounds which are inhibitors of thromboxane activity. In UK Patents 2039909, 2039480 and 2081258 compounds having such activity are described which contain a divalent cyclic group carrying a first side chain which is a 6-carboxyhex-2-enyl group or one of certain modifications thereof and a second side chain which may take a number of different forms. Among the possible different modifications of the 6-carboxyhex-2-enyl group which are mentioned in these patents is reduction of the double bond optionally accompanied by replacement of a carbon atom at the 1-, 2- or 3-position by a sulphur or oxygen atom. We have now found that compounds in which the 6-carboxyhex-2-enyl group is modified through the replacement of a carbon atom at the 5-position by oxygen or sulphur, optionally together with other modifications, show a valuable spectrum of activity and that this can involve an unexpected enhancement of biological activity either in terms of the level of activity and/or of variations in the nature of the activity at prostaglandin receptor sites as compared with the related compounds of the prior art.

Accordingly the present invention comprises a compound of formula (I)

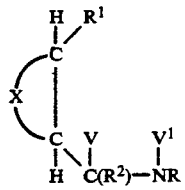
(I)

where

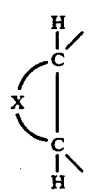

represents one of the divalent cyclic groups

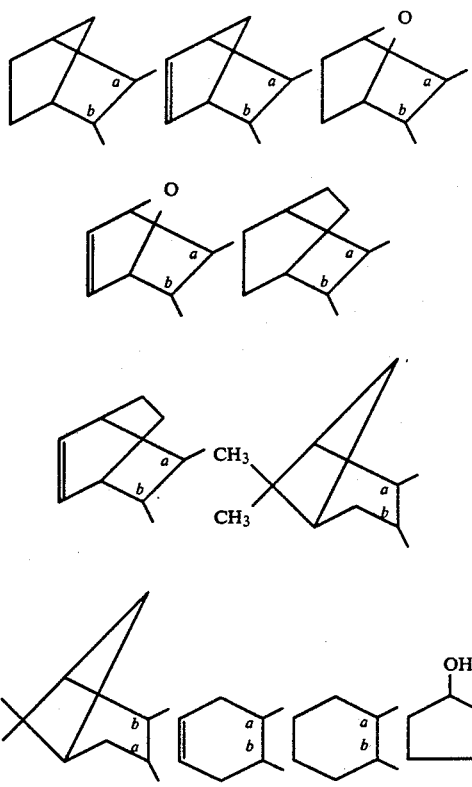

the letters a and b indicating in each case the points of attachment of the substituents $R^1$ and $CV(R^2)$—NV'R, respectively; $R^1$ is a group —$(CH_2)_b$—$(A)_a$—$(CH_2)_c$—B—$CH_2$—$CO_2R'$ in which A and B are each separately oxygen or sulphur, a is 0, b is 0 and c is an integer from 3 to 10, or a is 1, b is 0 or an integer from 1 to 7 and c is an integer from 2 to 9 with the sum of b and c being from 2 to 9, and $CO_2R'$ is a carboxy group or an amide, ester or salt derivative thereof; V and V' either each separately is hydrogen or together are the second bond of a carbon-nitrogen double bond; $R^2$ is hydrogen, an aliphatic hydrocarbon group or an aliphatic hydrocarbon group substituted by an aromatic group directly or through an oxygen or sulphur atom; and R is a group —$OR^3$, —$OR^4$, —D—$R^3$, —N=$R^5$ or —NW.G.W' in which D is —NH—, —NH.CS—, —NH.CO—, —NH.CO.CH$_2$N($R^6$)—, —NH.SO$_2$—, —NH.CO.NH—, —NH.CS.NH—, —NH.CO.O— or —NH.CS.O—, G is —CO— or —CS— and W and W' together are a group —$(CH_2)_d$— in which d is 3, 4, or 5, $R^3$ is an aliphatic hydrocarbon group, an aromatic group or an aliphatic hydrocarbon group substituted by one or more aromatic groups directly or through an oxygen or sulphur atom, $R^4$ is an aliphatic hydrocarbon group which is substituted through an oxygen atom by an aliphatic hydrocarbon group which is itself substituted directly by one or more aromatic groups, $R^5$ is an aliphatic hydrocarbon group, an aromatic group in which the $\pi$-electron system is not fully delocalised over the entire ring system, or an aliphatic hydrocarbon group substituted by one or more aromatic groups directly or through an oxygen or sulphur atom, and $R^6$ is hydrogen, an aliphatic hydrocarbon group, an aromatic group or an aliphatic hydrocarbon group substituted by one or more aromatic groups directly or through an oxygen or sulphur atom.

The various bridged ring systems indicated above may alternatively be represented in planar form, i.e. in the same order as

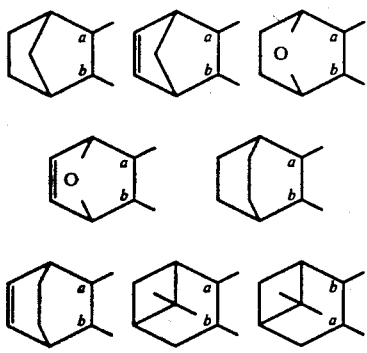

(the two free valancies in the centre of the last two formulae indicating methyl groups), but the more usual convention has generally been followed throughout the specification of representing these systems in non-planar form. It will be appreciated, however, that various stereoisomeric forms of the compounds (I) may be used in the invention. In particular, different geometric isomers can exist and most of these will occur in two enantiomorphic forms. For the bridged ring compounds (I) these two forms will have the structure illustrated hereinbefore and the mirror image of the structure. Taking the vicinally disubstituted bicyclo [2,2,1] heptane ring system as an example, such pairs of enantiomorphs may be shown as follows (the rings being numbered according to the system used herein).

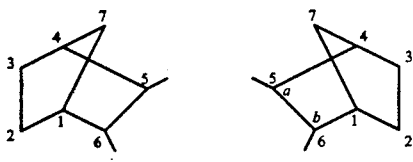

For the sake of added clarity it might be mentioned that alternative, equivalent, modes of showing these non-planar structures may be used. Thus the right hand of the two formulae shown directly above is equivalent to

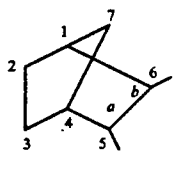

and also

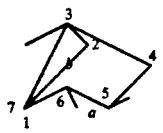

Variations in the group $R^1$ can involve the $-(CH_2)_b-(A)_a-(CH_2)_c-B-CH_2-$ chain or the terminal $-CO_2R'$ group. It is preferred that a is 0 and that B is oxygen. However, when a is 1, A and B are conveniently each sulphur or, more especially, oxygen and a good level and spectrum of activity has been observed in such compounds having a=1. Chains of a total of between 5 and 8 or 10 atoms terminally substituted by a carboxy group or a derivative thereof are of most interest with a preference for chains of at least 6 atoms. Compounds containing a chain of 7 atoms have shown an equally good level of activity as those containing a chain of 6 atoms, this being the chain length of the 6-carboxyhex-2-enyl group occurring in natural prostaglandins. There is therefore some interest in chains longer than the natural length. When a is 0, therefore, c is preferably 3, 4, 5, 6 or 7, particularly 4, 5 or 6. When a is 1, b+c is preferably 2, 3, 4, 5 or 6, particularly 3, 4 or 5, and it is also preferred that b is greater than 0 and that c is 2 or 3, the compounds in which a is 1 which are of particular interest being those which c is 2 and b is 1, 2 or 3 and those in which c is 3 and b is 0 or especially 1 or 2.

As regards the terminal group $-CO_2R'$, the carboxy group derivatives may be (i) esters, especially alkyl esters, for example those containing a $C_1-C_{10}$ alkyl group but particularly methyl or ethyl esters; (ii) amides, which may contain a group $-CONH_2$ or such a group in which the nitrogen atom is substituted, especially by one or two groups selected from substituted or unsubstituted phenyl groups, for example as described hereinafter, alkyl groups, for example $C_1-C_{10}$ alkyl groups, and from more complex groups such as $-SO_2CH_3$ or an analogue thereof containing a $C_2-C_{10}$ alkyl group, for example to provide a group of the form $-CONHSO_2CH_3$; and (iii) salts with various physiologically acceptable cations. Salt derivatives are of especial interest, specific examples of salts being those formed with an alkali metal such as sodium or with quaternary ammonium ions or amines such as tris (the symbol tris represents the compound 2-amino-2-hydroxymethylpropane 1,3-diol). It will be appreciated that many of such compounds in which the carboxy group is in derivative form are in fact bioprecursors for the corresponding compound containing a carboxy group to which they are converted in vivo.

Examples of specific groups $R^1$ are $-(CH_2)_4-O-CH_2-CO_2H$, $-(CH_2)_6-O-CH_2-CO_2H$ and especially $-(CH_2)_5-O-CH_2-CO_2H$, and also $-CH_2-O-(CH_2)_2-O-CH_2-CO_2H$, $-(CH_2)_3-O-(CH_2)_2-O-CH_2CO_2H$, $-(CH_2)_2O-(CH_2)_3-O-CH_2-CO_2H$, and especially $-(CH_2)_2-O-(CH_2)_2-O-CH_2CO_2H$ and $-CH_2-O-(CH_2)_3-O-CH_2-CO_2H$, as well as amide, ester and salt derivatives thereof.

Although the group $CV(R^2)-NV'R$ of the compounds (I) may take either the form $CH(R^2)-NHR$ or the form $C(R^2)=NR$ for all groups R, compounds of the first form are of relatively less interest when R is $-N=R^5$ or $-NW.G.W'$. Moreover, in general, with the first form there is a preference for those compounds in which $R^2$ is hydrogen. The second form is of interest across the whole range of compounds. However, as discussed hereinafter, certain groups R are of particular interest for both the form $CH(R^2)-NHR$ and the form $C(R^2)=NR$. It should be noted, however, that conversion of compounds of the first form to those of the second form has been observed in solution and it is possible that the biological activity of compounds of the first form might be attributable to the occurrence of a similar conversion in vivo.

Compounds in which the group $R^2$ is not hydrogen more usually contain aliphatic and araliphatic groups of the type described hereinafter in relation to the group $R^3$, aliphatic hydrocarbon groups substituted directly by an aromatic group, for example an unsubstituted or substituted phenyl or pyridyl group, and particularly unsubstituted aliphatic hydrocarbon groups being of most interest. When the group $R^2$ contains an aliphatic hydrocarbon group directly substituted by an aromatic group, then it is preferred that the aromatic group is not attached to a carbon atom of the aliphatic group which is itself attached directly to the carbon atom of the group $CV(R^2)$—$NV'R$. Thus, for example, a 2-phenylethyl group is preferred to a 1-phenylethyl or phenylmethyl (benzyl) group. The size of the group $R^2$ can however influence the ease with which the compounds may be prepared and $R^2$ is preferably either hydrogen or one of the smaller alkyl groups, for example of 1 to 3 carbon atoms, in substituted form, or particularly in unsubstituted form, for example ethyl and especially methyl.

Among the groups $CV(R^2)$—$NV'R$, those which terminate in a group $R^3$ are of particular interest. As indicated hereinbefore, the group $R^3$ can be of various forms. Aliphatic hydrocarbon groups constituting $R^3$ may conveniently be acyclic or cyclic and of one to five, six, seven, eight, nine, ten, eleven, twelve or even more carbon atoms. Saturated groups are of particular interest, for example an alkyl group which may be branched or unbranched such as methyl, ethyl, propyl, butyl, t-butyl, isobutyl, amyl, hexyl, isohexyl, heptyl, 4,4-dimethylpentyl, octyl, 2,2,4-trimethylpentyl, nonyl, decyl, undecyl and dodecyl, a cycloalkyl group such as cyclopentyl, cyclohexyl and cycloheptyl, and combinations of alkyl and cycloalkyl groups such as cyclohexylmethyl. Groups such as cyclohexylmethyl and alkyl groups of 5 to 10 carbon atoms are of some particular interest. Aliphatic hydrocarbon groups $R^3$ are perhaps of most interest when the group $CV(R^2)$—$NV'R$ has the form $CH(R^2)$—$NHR$, for example in compounds in which R is —$OR^3$, —$OR^4$, —$NHCOR^3$, —$NHCSR^3$, —$NHCONHR^3$, —$NHCSNHR^3$, —$NHCOOR^3$ or —$NHCSOR^3$.

In general, however, aromatic groups constituting $R^3$ are of greater interest than the unsubstitued aliphatic hydrocarbon groups and may be hydrocarbon or heterocyclic groups which may be unsubstituted or substituted. Moreover, the term 'aromatic group' as used herein extends to groups derived from ring systems having aromatic properties but in which the $\pi$-electron system is not fully delocalised over the entire ring system, such groups including those derived from fluorene and the dibenzocyclohexanes and dibenzocycloheptanes, such as 1,2,4,5-dibenzocyclohexane and 1,2,4,5-dibenzocycloheptane, and from dihydrobenzoxazole, dihydrobenzthiazole, N-methyldihydrobenzoxazole and N-methyldihydrobenzthiazole. The heterocyclic groups, which conveniently contain one, two or more similar or different nitrogen, oxygen or sulphur atoms, are more generally linked through a carbon atom so that, in the case of a pyridyl group, for example, pyrid-2-yl, pyrid-3-yl and pyrid-4-yl are of particular interest. Moreover, in the case of those groups containing one or more benzene rings together with one or more non-benzenoid rings, such as those derived from fluorene and from the dibenzocyclohexanes and dibenzocycloheptanes, and from benzthiazole, dihydrobenzthiazole, N-methyldihydrobenzthiazole and their benzoxazole analogues, linkage of the group is more usually effected through a non-benzenoid ring.

Among the aromatic groups constituting $R^3$, aromatic hydrocarbon groups, for example napthyl (including both napth-1-yl and napth-2-yl) and particularly phenyl, are however generally of rather greater interest than heterocyclic groups. Both aromatic hydrocarbon and heterocyclic groups may be substituted by one or more of various types of substituent, particularly by alkoxy groups, for example those containing alkyl groups of one, two, three or more carbon atoms as described above and especially methoxy, and by substituents being or containing a halogen residue, for example halogen groups such as bromo, chloro and especially fluoro, and also halogeno-substituted alkyl groups such as $CF_3$. Examples of other substituents are sulphamoyl groups which may optionally be N-substituted, amino groups which may be free or substituted, for example dimethylamino, hydroxyl, nitro and alkyl groups, for example of 1 to 3 carbon atoms or otherwise as described above. Substitution may be present at one or more of the ortho, meta and para positions of a phenyl ring or at a combination of two or more such positions (including two ortho or two meta positions), for example at the 2,4- or 3,4-positions. In the case of some substituants, for example nitro, aromatic groups containing a single substituent group may be of particular interest but in other cases substitution by more than one substituent may be of equal or greater interest. It will be appreciated that, in general, substitution and the position of substitution, for example by alkoxy groups and groups being or containing a halogen residue, may have a definite effect upon the level of activity of a compound.

Also of considerable interest, are groups $R^3$ which are aliphatic hydrocarbon groups substituted by one or more aromatic groups directly and/or through a sulphur or particularly an oxygen atom. Such groups, particularly those involving direct substitution, and also especially the unsubstituted aliphatic hydrocarbon groups $R^3$, are of greater interest than aromatic hydrocarbon groups $R^3$ in the case of compounds in which R is —$NH.CO.O$—$R^3$ or —$NH.CS.O$—$R^3$. The aliphatic groups may be of a similar size to those described above but preferably comprise an acyclic group, conveniently of 3 carbon atoms, particular of 2 carbon atoms and especially of 1 carbon atom, although this acyclic group may carry a cycloalkyl group as well as an aromatic group. Preferred acyclic groups thus take the form of unbranched alkylene groups such as methylene, ethylene or propylene which link the group $C(R^2)=N$— and the aromatic group, or corresponding trivalent groups of similar size. Similar aromatic hydrocarbon and heterocyclic residues are generally of interest for attachment to the aliphatic groups as have already been described above, the aromatic hydrocarbon groups again generally being of rather more interest than the heterocyclic groups. One group $R^3$ containing an aliphatic hydrocarbon group substituted by an aromatic group which is worth particular mention, in addition to those containing phenyl and substituent phenyl groups, is that consisting of an ethyl group substituted at the 1-position by a napthyl group, for example a napth-1-yl group. The reagent $N_2N.NH.CO.NHCH(CH_3)$-napth-1-yl, which may be used to prepare compounds (I) containing such a group, is of particular interest since it contains an asymmetric carbon atom and may be obtained in optically active form. Heterocyclic groups, where used, are of most interest in this context when linked to the aliphatic hydrocarbon group through a hetero atom, as for example in pyrid-1-yl. Substitution of an aliphatic hydrocarbon group, particularly terminally, by two or even three aromatic groups, for example phenyl, is of particular interest whilst also of interest are acyclic groups carrying terminally both an aromatic group, for example phenyl, and a cycloalkyl group, for example cyclohexyl. Other substituted aliphatic hydrocarbon groups of especial note, although perhaps less so in the case of groups of the form $CH(R^2)$—NHR, are those which are substituted by an aromatic group through a sulphur or particularly an oxygen atom. In this case, however, the relative instability of the linkages —O—CH$_2$—S— and —O—CH$_2$—O— must be borne in mind so that, for example, with some forms of group $CV(R^2)$—NV'R any aliphatic hydrocarbon group substituted through oxygen or sulphur is conveniently of at least 2 carbon atoms. Moreover, with groups $R^3$ consisting of an aliphatic hydrocarbon group substituted by more than one aromatic group, these preferably do not have more than one of the aromatic groups attached to the same carbon atom through oxygen or sulphur.

When the group $R^3$ is or contains a substituted aromatic group, some positions of substitution may be of more interest than others in particular cases. Thus, for example, when $R^3$ is a substituted benzyl group the order of interest is often o−p>m, when $R^3$ is a substituted phenyloxyethyl group it is o>m>p, and when $R^3$ is a substituted phenyl group it is m−p>o. It will be appreciated that, particularly when two positions are of similar interest, it may be of value to have a substituent at each position as when the group $R^3$ is 3,4-dimethoxyphenyl.

Among the various groups R which terminate in a group $R^3$, those of particular interest are the groups in which R is a group $OR^3$ or a group —D—$R^3$ in which D is —NH.CO—, —NH.CS—, —NH.CO.O—, —NH.CS.O—, —NH.SO$_2$— or especially —NH.CO.NH— or —NH.CS.NH—. Especially good levels of activity result with compounds in which R is a group —$OR^3$ or particularly a group —NH.CO.NHR$^3$ and especially a group —NH.CS.NHR$^3$. Among various groups of the form $C(R^2)=NR$ in which R terminates in a group $R^3$, those in which $R^3$ is an aliphatic hydrocarbon group are perhaps of rather less interest than the others, groups $R^3$ which are aliphatic hydrocarbon groups substituted by one or more aromatic groups directly or through an oxygen or sulphur atom being of somewhat greater interest when R is a group —$OR^3$ and groups $R^3$ which are aromatic groups being of somewhat greater interest when R is a group —D—$R^3$.

Examples of specific groups $R^3$ are:

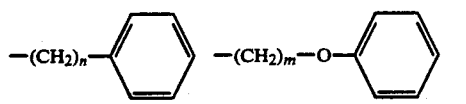

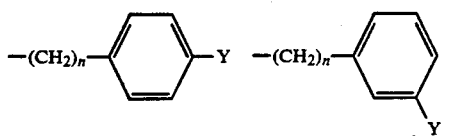

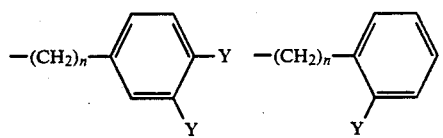

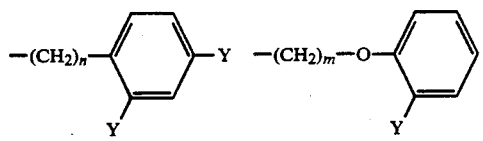

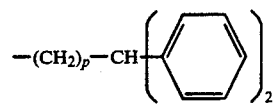

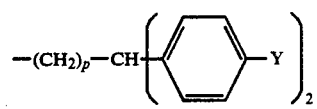

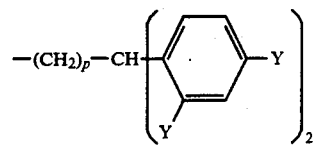

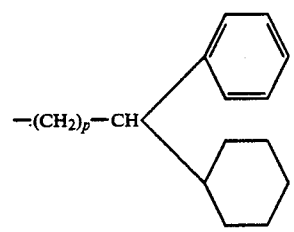

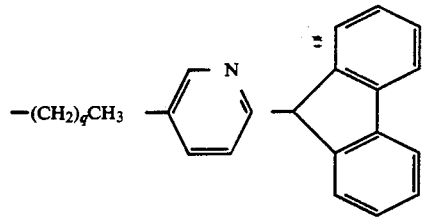

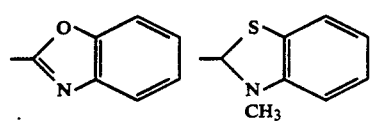

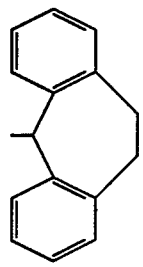

wherein n=0, 1, 2 or 3, m=1, 2 or 3, p=0, 1 or 2, q=1, 2, 3, 4 or 5 and Y=OCH₃, Cl, F, CF₃ or CH₃ (preferences between ortho, meta and para substitution in various cases according to the value of n being indicated hereinbefore).

In addition to compounds containing O-substituted oxime groups of the CV(R²)—NV'(OR³) type which are discussed above, the invention also includes compounds containing O-substituted oxime groups of the type CV(R²)—NV'(OR⁴). The group R⁴, as indicated above, is an aliphatic hydrocarbon group which is substituted through an oxygen atom by an aliphatic hydrocarbon group which is itself substituted directly by one or more aromatic groups and preferences as regards both aliphatic hydrocarbon groups and the aromatic groups are broadly as expressed above in the case of the group R³. In particular, the aliphatic hydrocarbon group attached to the oxime oxygen atom is preferably of more than one carbon atoms, for example being of 3 or particularly 2 carbon atoms, whilst the aliphatic hydrocarbon group substituted by one or more aromatic groups is preferably of 1 to 3 carbon atoms, for example 1 carbon atom. This latter aliphatic hydrocarbon group may conveniently be terminally substituted by one, two or even three aromatic groups although two or only one aromatic group are preferred and these may conveniently be phenyl groups or substituted phenyl groups as described above in relation to R³.

As well as compounds (I) containing a group CV(R²)—NV'R terminating in a monovalent group R³ or R⁴ other compounds (I) of some interest contain a group CV(R²)—NV'R in which R is —N=R⁵, R⁵ being a divalent organic group as defined above. Unsubstituted and substituted aliphatic hydrocarbon groups R⁵ most usually are groups similar to those described above in relation to R³ but which contain two free valencies at the point of linkage. In the case of groups R⁵ which are aromatic groups it will be appreciated that there will not be such a close correspondence to the groups R³ described above as these aromatic groups, because of their divalent nature, cannot derive from many of the aromatic systems described above in which the π-electrons are fully delocalised over the whole ring system, such as those comprising a single benzene or pyridine ring. Such aromatic groups constituting R⁵ are therefore of the type described hereinbefore in which the π-electron system is not fully delocalised over the entire ring system and, indeed, this type of residue is one of those preferred in the case of R⁵, specific preferences among such types of aromatic group being as discussed above in relation to R³. Another preferred type of group R⁵ is a methylene group in which both hydrogen atoms are substituted by an aromatic group, for example such as phenyl, so that, in the preferred case for such groups R where V and V' together represent the second bond of a carbon-nitrogen double bond, the double bonds of the C(R²)=N—N=C< system are in conjugation with the aromatic system. Examples of specific groups R⁵ are:

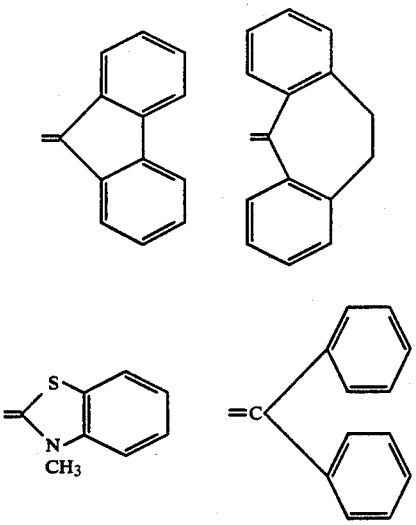

As regards the group R⁶ which constitutes a part of a group —D—R³ of the specific type

the preferences among aliphatic, aromatic and araliphatic groups R⁶ generally correspond to those indicated above for R³ although aliphatic hydrocarbon groups are of rather more interest than is generally the case and, with the araliphatic groups, direct substitution by an aromatic group is preferred to substitution through an oxygen or sulphur atom. Moreover, an important additional alternative is for R⁶ to be hydrogen. Conveniently the group

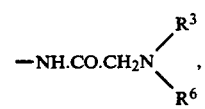

either contains a group R⁶ which is identical to the group R³, for example both being an unsubstituted aliphatic hydrocarbon group or one substituted directly by an aromatic group, or a group R⁶ which is hydrogen. Thus, specific examples of the larger group are —NH.CO.CH₂N(CH₂C₆H₅)₂, —NH.CO.CH₂N(C₂H₅)₂, and —NH.CO.CH₂NH(CH₂C₆H₅).

Compounds of use in the present invention may contain, in the order previously illustrated, one of the following types of ring system: bicyclo [2,2,1] heptane, bicyclo [2,2,1] hept-2Z-ene, 7-oxa-bicyclo [2,2,1] heptane, 7-oxa-bicyclo [2,2,1] hept-2Z-ene, bicyclo [2,2,2] octane, bicyclo [2,2,2] oct-2Z-ene, 6,6-dimethyl-bicyclo [3,1,1] heptane, cyclohexene, cyclohexane and hydroxycyclopentane, the 6,6-dimethyl-bicyclo [3,1,1] heptane ring system, unlike the others, being substituted in either of two ways, corresponding to reversal of the substituents shown at the a and b positions. It will be appreciated that the bridged ring systems present in compounds according to the present invention show a range of degrees of asymmetry. The 6,6-dimethyl-bicyclo [3,1,1] heptane ring system is sufficiently asymmetric for reversal of the substituents at the a and b positions to result in a different structural isomer, and thus a different compound (I), both types of compound (I) containing the 6,6-dimethyl-bicyclo [3,1,1] heptane ring system being of use in the present invention. In the case of the bicyclo [2,2,1] heptane and bicyclo [2,2,1] hept-2Z-ene ring systems and their 7-oxa analogues, however, reversal of these substituents would merely provide a structure which represents an alternative stereoisomer, the invention, as has previously been indicated, extending to the use of the compounds (I) in their various stereoisomeric forms. The situation with the bicyclo [2,2,2] oct-2Z-ene ring system is similar to that pertaining in the case of its 7-membered analogue but the bicyclo [2,2,2] octane ring system has a sufficient degree of symmetry for such reversal of the a and b substituents to give the same compound (I) of identical stereochemistry. Among these ring systems, the bridged ring systems are of particular interest and, of those which may be saturated or unsaturated, the former are usually preferred, particularly in the case of the compounds containing an oxygen bridging group, as unsaturation generally confers lower stability whilst the level of biological activity is generally substantially similar. The bicyclo [2,2,1] heptane and especially the bicyclo [2,2,2] octane (which may often exhibit higher activity) ring systems may be mentioned as of particular interest, and also to a somewhat lesser extent the corresponding unsaturated ring systems. The 6,6-dimethyl-bicyclo [3,1,1] heptane ring system is in general of somewhat lesser interest than the other bridged ring systems, preliminary biological activity test data suggesting a somewhat lower level of activity for this ring system as compared with the bicyclo [2,2,1] heptane ring system.

It will be appreciated that the structures of the compounds described above provide various opportunities for the occurrence of stereoisomerism. Thus, the substituent groups $R^1$ and $CV(R^2)$—$NV'R$ may be in the cis or trans relationship to each other, compounds of the latter configuration more generally being preferred although cis compounds (particularly in the 5-exo, 6-exo rather than the 5-endo, 6-endo form, referred to below, where appropriate) are not without interest, especially in the case of the cyclohexane, cyclohexene and the two oxygen bridged ring systems. Moreover, when the ring system is one which is bridged or contains a hydroxy substituent then, in most cases, different isomers will exist which vary according to the way in which the substituent groups $R^1$ and $CV(R^2)$—$NV'R$ are disposed in relation to the bridging groups or the substituent. Isomers of particular interest are shown below in one of the two enatiomorphic forms which can generally exist in each case, the other enantiomorph having a structure which is the mirror image of that shown. The unsaturated ring system is illustrated where the ring system may be saturated or unsaturated, the symbol B' representing —CH$_2$— (position 7), —O— (position 7) or —CH$_2$CH$_2$— (positions 7 and 8), and the substituent at position b is shown as $C(R^2)$=NR. The cis isomers can of course also generally exist in two forms for these same ring systems, for example the 5-exo, 6-exo and 5-endo, 6-endo forms for the ring systems containing a group B', each of which forms can again exist as either of two enantiomers. As indicated above, the bicyclo [2,2,2] octane system possesses a greater degree of symmetry than the other bridged ring systems as the two bridging groups attached together at the bridge positions (1 and 4) are identical, both being —CH$_2$CH$_2$—. In this case, therefore, although the trans isomer is preferred and can exist in two enantiomorphic forms, the endo, exo type of isomerism which can occur with the other bridged ring systems cannot arise.

It will be seen that in the structures shown below the numbering applied herein to the various positions of the ring system has been indicated. It should be noted that the system of numbering adopted for the bridged ring systems which can exist in both unsaturated and saturated form is chosen so that the double bond in the unsaturated ring system receives the lowest number possible (2), the substituents $R^1$ and $C(R^2)$=NR or [CH($R^2$)—NHR] then being at the 5- and 6-positions respectively. For conformity, a similar system of numbering is followed for the analogous saturated ring systems, the substituents again being described as at the 5- and 6-, rather than the 2- and 3-positions as in the 6,6-dimethyl [3,1,1] heptane system.

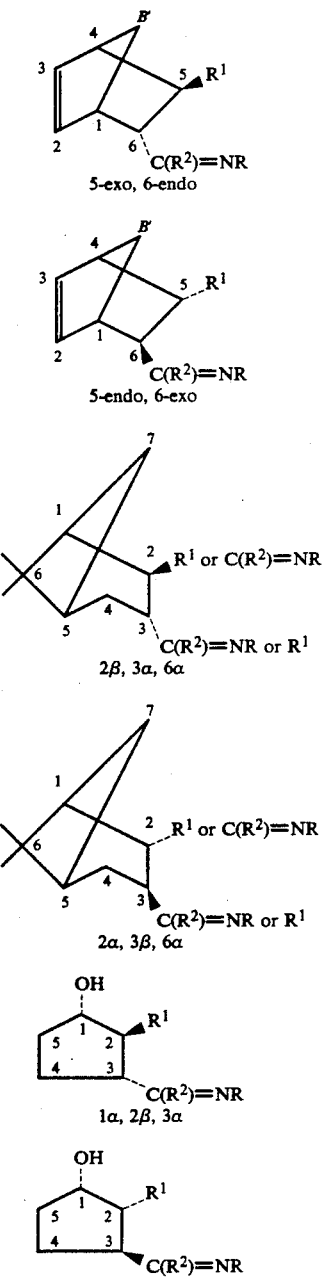

1α, 2α, 3β

Among the isomers illustrated above, of the two forms shown in each case one is usually preferred to a somewhat greater extent than the other. In the case of the 5-exo, 6-endo and 5-endo, 6-exo isomers the latter is most usually preferred but in the case where B' is —O— the 5-exo, 6-endo isomer may be of equal or greater interest. In the case of the 2β, 3α, 6α and 2α, 3β, 6α, 6α isomers the latter is of most interest. [The convention applied herein for naming the compounds (I) containing a 6,6-dimethyl-bicyclo [3,1,1] heptane ring system is the use of α and β to indicate the directions in which the substituents at the 2- and 3-positions are directed. In the designations used above the position of the bridging carbon atom at position 6 has for simplicity has also been indicated by an α or a β (the position of the gem dimethyl groups at the 6-position is dictated by that of the carbon atom to which they are attached).] In the case of the 1α, 2β, 3α and 1α, 2α, 3β isomers the latter is again of most interest.

When the substituent $CV(R^2)$—$NV'R$ is of the form $C(R^2)$=$NR$, syn and anti isomerism is possible about the carbon-nitrogen double bond but the isomers may often be readily interconvertible at room temperature and thus difficult to separate, existing as a mixture which shows biological activity that may, however, derive predominantly from one isomer. In addition to the foregoing isomerism, as indicated previously the compounds of the present invention will in most cases additionally be resolvable into enantiomorphic forms and one among these may be preferred by virtue of biological activity or physical properties. Single enantiomers may be obtained either by the use of an optically active starting material or by resolution of a pair of enantiomorphs.

Examples of specific compounds (I) which may be used in the present invention include the compound (Ia)

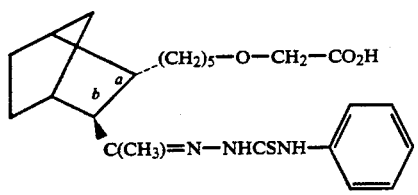

(Ia)

and related compounds in which one or more of the following variations is present: (a) the converse trans stereochemical arrangement of the substituents at a and b; (b) one of the other divalent cyclic groups described hereinbefore in place of the bicyclo [2,2,1] heptane group, for example a bicyclo [2,2,2] octane group; (c) a 6-carboxy-5-oxahexyl group in place of the 7-carboxy-6-oxaheptyl group; (d) derivatisation of the carboxy group as an amide, ester or salt and (e) a grouping —CH=N—, —CH$_2$NH—, —CH(CH$_3$)—NH—, —C(C$_2$H$_5$)=N— or —CH(C$_2$H$_5$)—NH— in place of the grouping —C(CH$_3$)=N—; (f) a grouping —NHCONH—C$_6$H$_5$ or —O—CH$_2$—(C$_6$H$_5$)$_2$ in place of the —NHCSNH—C$_6$H$_5$ grouping; (g) in the compound Ia or in a modification (f) thereof, a n-hexyl or n-heptyl group or a phenyl group which is substituted, for example by one or more substituents which are selected from alkyl, alkoxy, amino, halogeno, halogeno-substituted alkyl, nitro and sulphamoyl groups, in place of the unsubstituted phenyl group.

One group of compounds (Ia) of some particular interest in view of their activity contain any one of the ring systems, but particularly a bicyclo [2,2,1] heptane or especially a bicyclo [2,2,2] octane ring system (or their respective unsaturated analogues), substituted at the 5-position (particularly in a trans stereochemical arrangement and especially in the 5-endo, 6-exo or like configuration) by a 7-carboxy-6-oxaheptyl or especially a 6-carboxy-5-oxahexyl group, or a derivative thereof, and at the 6-position by a N-(phenylcarbamoyl)-hydrazonomethyl, 1-[N-(phenylcarbamoyl)-hydrazono]-propyl or especially a 1-[N-(phenylcarbamoyl)-hydrazono]-ethyl group or, more particularly, by a N-(phenylthiocarbamoyl)-hydrazonomethyl, 1-[N-(phenylthiocarbamoyl)-hydrazono]-propyl or especially a 1-[N-(phenylthiocarbamoyl)-hydrazono]-ethyl group wherein the phenyl group is substituted by one or more groups selected from hydroxy and especially alkoxy groups, particularly methoxy groups, conveniently one such group being at the para position, for example to give a 2,4 or 3,4-dimethoxyphenyl group or particularly a p-methoxyphenyl group. A particular example of this preferred group of compounds is the compound trans-5-(6'-carboxy-5'-oxahexyl)-6-(1'-[N-(p-methoxyphenylthiocarbamoyl)-hydrazono]-ethyl)-bicyclo [2,2,2] octane, and carboxy group derivatives thereof.

A further group of compounds having activity at thromboxane receptor sites which have a structure related to that of the compounds of UK Patents 2039909, 2039480 and 2081250 referred to hereinbefore but which contain a different form of second side chain is described in UK Patent 2113678. It is possible to prepare compounds containing a first side chain corresponding to the group $R^1$ present in the compounds (I) and a second side chain corresponding to that present in the compounds of UK Patent 2113678. The present invention therefore also comprises a compound of formula (II).

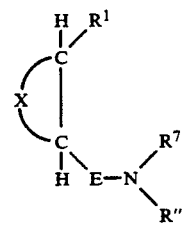

(II)

wherein

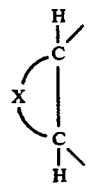

is as previously defined,

E is an aliphatic hydrocarbon group with a chain length between the points of attachment to the divalent cyclic group and to the group $NR^7R''$ of 1 to 5 carbon atoms or such a group substituted by an aromatic group; $R^7$ is hydrogen, an aliphatic hydrocarbon group, an aromatic group or an aliphatic hydrocarbon group substituted by an aromatic group or groups; and R" is a group —CO.NR$^8$R$^9$, —CS.NR$^8$R$^9$, —CNH.NR$^8$R$^9$, —CO.R$^9$ or —CS.R$^9$ in which R$^8$ is hydrogen, an aliphatic hydrocarbon group, an aromatic group or an aliphatic hydrocarbon group substituted by an aromatic group or groups, but with the proviso that at least one of R$^7$ and R$^8$ is hydrogen, and R$^9$ is an aliphatic hydrocarbon group, an aromatic group or an aliphatic hydrocarbon group substituted directly by an aromatic group or groups and/or through an oxygen or sulphur atom either by an aromatic group or by an aliphatic hydrocarbon group substituted directly by an aromatic group or groups.

Among these compounds of formula (II) preferences as to X and R$^1$ are as expresed hereinbefore in relation to the compounds of formula (I) whilst preferences as to the groups E, R$^7$ and R" are as expressed in UK Patent 2113678 (corresponding patent applications include U.S. application Ser. No. 531,899 and Japanese Application 83/500327) in relation to the groups A, R$^2$ and R, respectively, of the compounds (I) described therein and, as regards the groups R$^8$ and R$^9$, particularly when they are aliphatic hydrocarbon groups, as expressed hereinbefore for the groups R$^3$ of the compound (I). Preferences as to the stereochemistry of the compounds (II) are as expressed hereinbefore in relation to the compounds (I).

The compounds of formula (I) and (II) may in each case conveniently be prepared using an intermediate of formula (III)

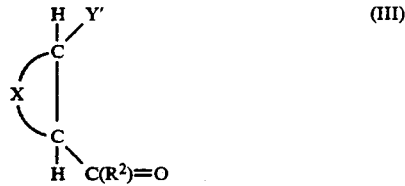

in which Y' represents R$^1$ as defined hereinbefore [the compound then being of formula (IIIa)] or a precursor therefor and X and R$^2$ are as previously defined for (I). Examples of specific compounds (IIIa) are those of formula (IIIb)

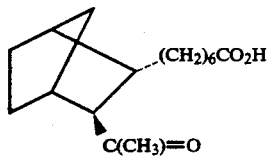

and related compounds in which one or more of the following variations is present: (a) the converse trans stereochemical arrangement of the substituents R$^1$ and C(CH$_3$)=O; (b) one of the alternative saturated or mono-unsaturated bridged groups described hereinbefore in place of the bicyclo [2,2,1] heptane group, for example a bicyclo [2,2,2] octane group; (c) a 7-carboxy-6-oxaheptyl or 6-carboxy-5-oxahexyl group in place of the 6-carboxyhexyl group; (d) derivatisation of the carboxy group as an amide, ester or salt; (e) an ethyl group in place of the methyl group. Examples of further specific compounds (IIIa) include those having a formula (IIIb) but with the group —C(CH$_3$)=O replaced by —CHO and related compounds in which one or more of the variations (a), (b), (c) and (d) indicated hereinbefore in relation to formula (IIIb) is present.

Such intermediates (IIIa), which are themselves novel compounds and are included within the scope of the present invention, may be prepared by modifications of the routes described in the four UK Patents 2039909, 2039480, 2081258 and 2113678 (corresponding patents and patent applications are, respectively, in the U.S. Pat. Nos. 4,430,345, 4,438,136 and 4,596,823 and U.S. patent application Ser. No. 531,899, and in Japan Patent Applications 80/500131, 80/500132, 81/502230 and 83/500327) referred to hereinbefore and in UK Patent Application 2119375 (corresponding U.S. patent application Ser. No. 374,125) and European Patent Applications 0094792 (corresponding U.S. patent application Ser. No. 378,560) and 010,7995 (corresponding U.S. patent application Ser. No. 436,741). These procedures involve reacting a compound of formula (IIIc)

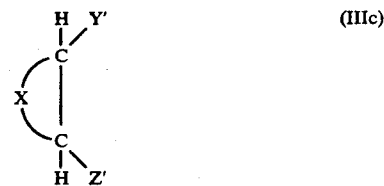

in which Z' represents (a) a hydroxymethyl group, (b) a formyl group in acetal form, or (c) a group CH(R$^2$)OH, Y' is either R$^1$ as defined for (IIIa) or a precursor for R$^1$, X is as defined for (IIIa) and R$^2$ is as defined for (IIIa) except that it may not be hydrogen, the said reaction consisting of (a) effecting oxidation of the hydroxymethyl group to give a formyl group, (b) effecting hydrolysis of the acetal to give a formyl group, or (c) effecting oxidation of the group CH(R$^2$)OH to give a group C(R$^2$)=O, and where appropriate converting the group Y' in the resultant product into a group R$^1$, the process optionally involving a change of stereochemistry of (IIIc) to that of (IIIa). It will be appreciated that of the procedures (a) and (b) one may usually be applied with certain ring systems and the other with other ring systems. Thus in the case of the preferred bicyclo [2,2,1] heptane and bicyclo [2,2,2] octane ring systems, and their unsaturated analogues, the more usual precursor for formyl group is a formyl group in acetal form. Furthermore, the compounds (III) in which R$^2$ is hydrogen as well as being of use as intermediates for the preparation of compounds (I) in which R$^2$ is hydrogen, also provide a precursor for the compounds (III) in which R$^2$ is an aliphatic or araliphatic group. Thus, effecting a Grignard reaction between the formyl group and a reagent R$^2$-Mg-Halogen yields a group CH(R$^2$)OH, wherein R$^2$ is other than hydrogen, which may be oxidised, for example using Jones reagent, to a group C(R$^2$)=O.

In addition to obtaining such intermediates by modifications of the processes described in the patents and patent application referred to above, an alternative route of particular value may be used which is the subject of a UK patent applications of even date herewithin in our name claiming priority from application 8600997 (and also of corresponding overseas applications) and which is applicable to compounds containing the bicyclo [2,2,1] heptane, bicyclo [2,2,1] hept-2Z-ene, 7-oxa-bicyclo [2,2,1] heptane, 7-oxa-bicyclo [2,2,1] hept-2Z-ene, bicyclo [2,2,2] octane, bicyclo [2,2,2] oct- 2Z-ene, cyclohexane and cyclohexane ring systems. The route involves the reaction of a diene and a dienophile to form as a Diels Alder adduct a compound (III) or a precursor readily convertible thereto. The route is illustrated below in reaction scheme (1) for a compound (III) in which the groups Y and C(R$^2$)=O are 6-ethoxycarbonyl-5-oxahexyl and acetyl respectively:

gent used in the Horner reaction may be varied through replacing the terminal acetyl group by an alternative acyl group R$^2$CO— or a formyl group in order to produce dienophiles providing a compound (III) containing an alternative group R$^2$. The third form of variation of the procedure shown involves the use of a different compound in the reaction with this phosphonate reagent to produce dienophiles providing a compound (III) containing an alternative group Y. Thus, it will be apparent that the use of a diol HO—CH$_2$—(CH$_2$)$_4$CH$_2$—OH will provide a compound (III) containing a 7-ethoxycarbonyl-6-oxaheptyl group Y. It has been found that the reaction of the diol HO—CH$_2$(CH$_2$)$_3$CH$_2$—OH with ethyl bromoacetate leads to a mixture of the desired compound HO—CH$_2$(CH$_2$)$_3$CH$_2$OCH$_2$CO$_2$Et and of the bromo compound HO—CH$_2$(CH$_2$)$_3$CH$_2$OCOCH$_2$Br. It is possible to treat this mixture with dihydropyran to form the respective tetrahydropyranyl ethers, then to hydrolyse the respective ester groups of these ethers and separate the two products by Et$_2$O extraction from an aqueous basic medium. The two separate ethers may then be reacted to remove the tetrahydropyranyl ether function and generate the appropriate functional group at the other end of each molecule. This procedure, which provides an alternative to the difficult separation of the compounds HO—CH$_2$(CH$_2$)$_3$CH$_2$OCH$_2$CO$_2$Et and HO—CH$_2$(CH$_2$)$_3$CH$_2$OCOCH$_2$Br, is illustrated below for the generalised use of a diol HO—(CH$_2$)$_r$—OH in which r is an appropriate integer and THPO is tetrahydropyranyloxy.

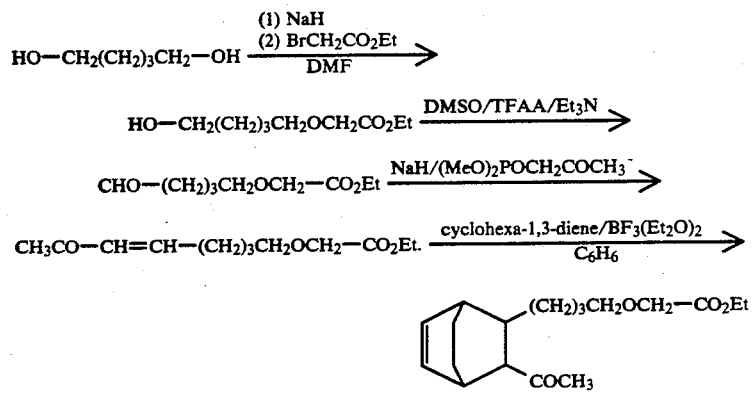

(1)

(In this reaction scheme conventional abbreviations are used in designating the reactants and solvents, i.e. Me: methyl; Et: ethyl; DMF: dimethylformamide; DMSO: dimethylsulphoxide; TFAA: trifluoroacetic acid anhydride.)

It will be appreciated that the ring system produced by such a procedure contains a double bond and that a reduction step will be required in order to produce a saturated ring system. It should be noted that the Horner reaction using the phosphonate reagent will generally provide a dienophile having the trans configuration about the carbon-carbon double bond so that this route is particularly adapted to the preparation of compounds in the preferred trans form, although the route can be used for the preparation of compounds (I) of the cis configuration if a different approach is used to provide a cis dienophile. Moreover, the Diels Alder reaction will lead to a mixture of the two trans or cis isomers which can exist in most cases and a separation will be necessary if one of these is required free from the other. This is not the case, however, with the bicyclo [2,2,2] octane, cyclohexane and cyclohexene ring systems which have a greater degree of symmetry and therefore exist in only one trans and one cis form (which do however each consist of two enantiomers). The route has the particular advantage that it may be used to produce directly an intermediate (III) containing the desired group Y, subject to modification of the terminal carboxy group from or to derivature form, rather than having to build up the group Y after construction of the ring system as in the other procedures. The Diels Alder reaction may use only heat but the reaction may be unacceptably slow and it is often more convenient to utilise a Lewis acid as a catalyst, for example alumium chloride or more preferably titanium tetrachloride, stannic chloride or especially boron trifluoride, although it is still also preferred to carry out the reaction at elevated temperature, for example at about 80° C.

It will be clearly apparent to those skilled in the art how the diene and dienophile used in the scheme shown above may be varied to produce different compounds (III). Thus, firstly, pentadiene, furan or 1,3-butadiene can be used in the final step as the diene in place of cyclohexa-1,3-diene. Secondly, the phosphonate rea-

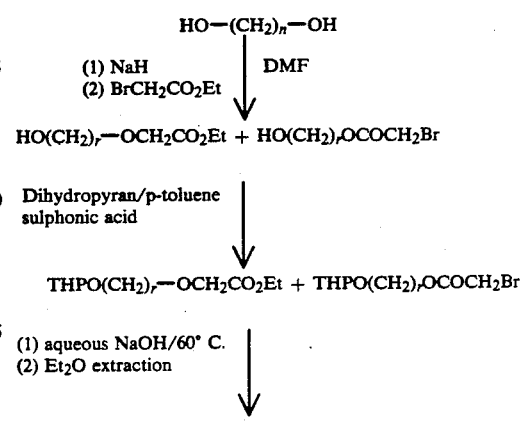

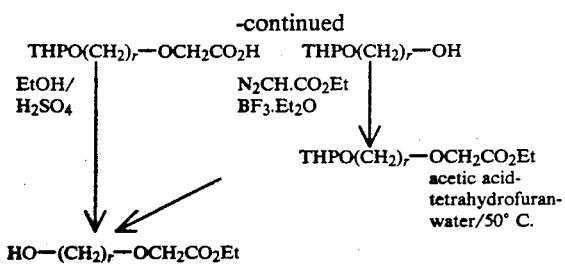

A further variation of the scheme (1) of particular interest leading to groups Y containing two oxygen atoms is illustrated in reaction scheme (2) below.

taining a formyl group will usually be prepared and then converted to the compound containing the desired group $C(R^2)=O$ through a Grignard reaction followed by oxidation of the product.

A suitable route for the preparation of compounds (III) containing two oxygen and/or sulphur atoms in the chain of the group $R^1$, which may be applied to the whole range of ring systems including the bicyclo [3,1,1] heptane ring system, is illustrated below for the case where two oxygen atoms are present. Only the group $R^1$ is shown, the group $C(R^2)=O$ suitably being protected as an acetal, which may conveniently be a cyclic acetal such as that obtained with ethylene glycol, the oxo group being regenerated by acid hydrolysis at (2)

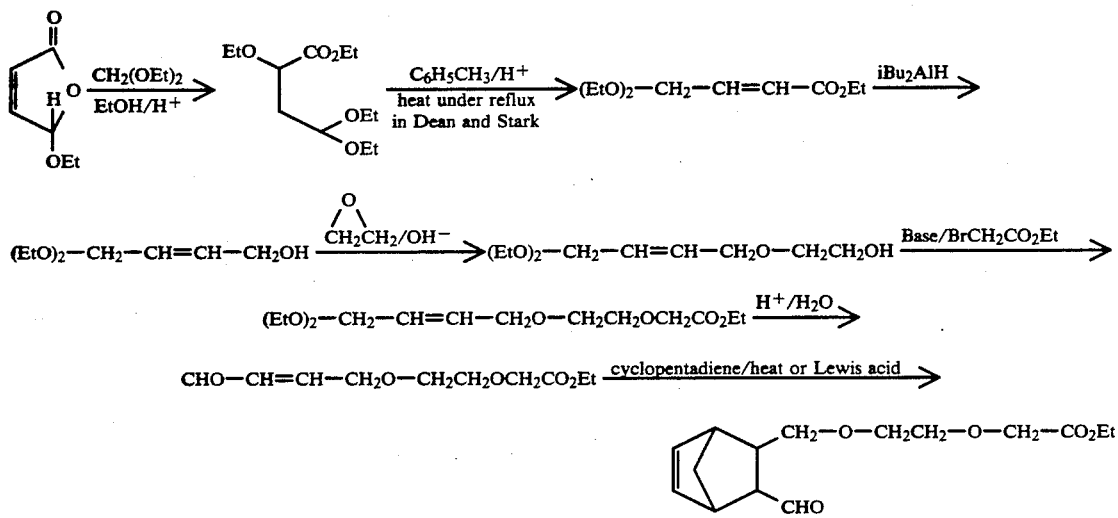

(in a reaction such as that with $(EtO)_2$—$CH_2$—$CH=CH$—$CH_2O$—$CH_2CH_2OH$ where only one reactive functional group is present the ethyl bromoacetate may conveniently be replaced by ethyl diazoacetate). The procedure can be varied through chain extension of the compound $(EtO)_2$—$CH_2$—$CH=CH$—$CH_2OH$, for example via the corresponding nitrile, before the reaction with ethylene oxide. Thus, for example, a single chain extension will give an aldehyde/ester $CHO$—$CH=CH$—$CH_2CH_2O$—$CH_2CH_2OCH_2CO_2Et$ providing compounds (III) containing a 7-ethoxycarbonyl-3,6-dioxaheptyl group Y. A further variation of the procedure involves the conversion of the formyl group of the aldehyde/ester to an acyl group, for example an acetyl group. Various approaches for doing this are possible but conveniently the formyl group is oxidised to a carboxy group which is then converted to the acid chloride and this is in turn converted to a group $R^2CO$—, for example using the appropriate cadmium compound $(R^2)_2Cd$, dimethyl cadmium providing an acetyl group.

The preparation of compounds containing the 6,6-dimethylbicyclo [3,1,1] heptane and hydroxycyclopentane systems is most conveniently effected by modifications of procedures described in UK Patent 2081258 for the preparation of compounds with a side chain having an oxa group at the 3-position, for example by chain extension of (−)-myrtenol or (−)-nopol, or by modifications of procedures described in European Patent 0044711. With these rings systems, when a compound containing a group $R^2$ other than hydrogen is required, the corresponding intermediate compound (III) conthe end of the series of reactions.

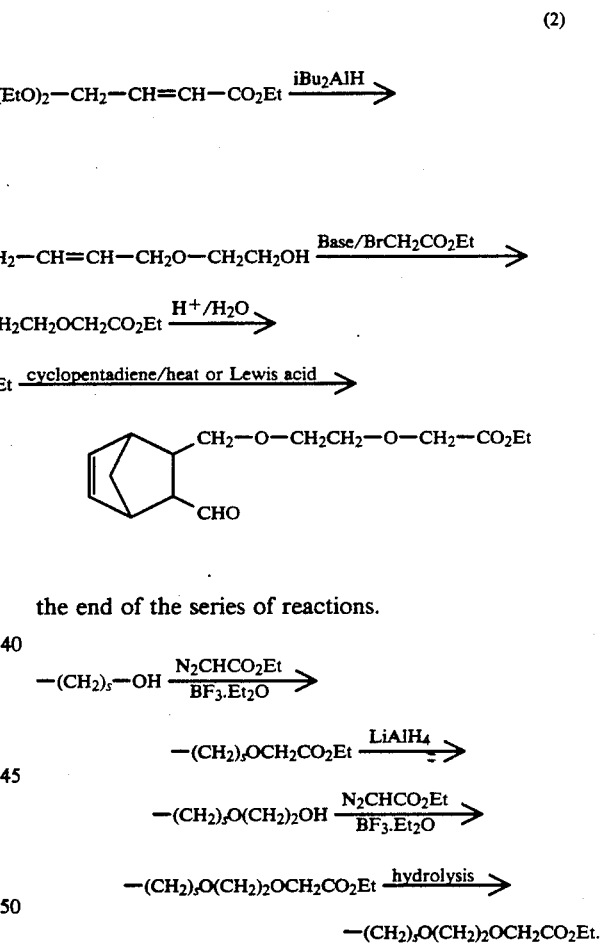

In the above scheme the symbol s represents an appropriate integer, the case where s is 1 being illustrated in Example 9 and the case where s is 2 in Example 12.

Compounds containing thio rather than oxa groups can be prepared by modifications of the procedures described for the latter, for example employing analogous sulphur-containing reagents. Groups Y' in compounds (III) which do not correspond directly to $R^1$ usually contain a group Y' terminating in a carboxy group in derivative form when $R^1$ terminates in a carboxy group in free acid form and vice versa. Esters, amides and salts may all be prepared by conventional procedures for example by reaction with the appropriate alcohol for esters or alternatively with diazomethane for methyl esters, and free carboxy groups may be generated by the hydrolysis of esters or amides and the acidification of salts, again using conventional procedures. It should be noted that compounds containing an oxygen or sulphur atom in the group $R^1$ in a position beta to the carboxy group may often particularly readily undergo ester formation, for example even simply on solution in an alcohol such as ethanol. It will be appreciated that the methods described above for the preparation of the compounds (I), (II) and (III) are not the only ones which may be used for the preparation of these compounds and that various alternative procedures may be used as will be apparent to those skilled in the art of prostaglandin chemistry.

In the case of the compounds of formula (I), these may be obtained from the intermediate (III) by reacting it with a reagent $ZNH_2$, Z being either R or a precursor for R, using procedures described in UK Patents 2039909, 2039480 and 2081258, and where appropriate converting the group Y and/or the group Z in the resultant product into the groups $R^1$ and R, respectively. In the case of compounds (I) in which the group $CV(R^2)$—$NV'R$ is of the form $C(R^2)$=$NR$, this group can usually be formed through direct reaction of the group $C(R^2)$=$O$ of the intermediate compound (III) with a reagent $RNH_2$. Thus, the compounds in which R is —NH.CS.NH—$R^3$ are readily obtained by reaction with the appropriate thiosemicarbazide $H_2N.NH.CS.NH.R^3$. These procedures are described particularly in UK Patents 2039909, 2039480 and 2081258 and in UK Patent Application 2119375. In the case of compounds (I) in which the group $CV(R^2)$—$NV'R$ is of the form $CH(R^2)$—$NHR$, the compound containing the corresponding group $C(R^2)$=$NR$ is most usually prepared first and then reduced to the desired compound. Various methods of reduction are available, the choice depending largely upon whether the compound contains any carbon-carbon double bonds. When this is not the case hydrogenation using palladium/charcoal or a like catalyst is appropriate but when a carbon-carbon double bond is present in the ring a reducing agent such as sodium cyanoborohydride is required which will not effect reduction of that carbon-carbon double bond. If desired, it is possible to prepare compounds (I) containing a saturated bicyclo [2,2,1] heptane, 7-oxa-bicyclo [2,2,1] heptane or bicyclo [2,2,2] octane ring systems and a group $CV(R^2)$—$NV'R$ of the form $CH(R^2)$—$NHR$ through the reduction of the corresponding bicyclo [2,2,1] hept-2Z-ene, 7-oxa-bicyclo [2,2,1] hept-2Z-ene or bicyclo ([2,2,2] oct-2Z-ene containing side chains Y and $C(R^2)$=$NR$ followed, where appropriate, by the conversion of Y to the desired group R'. These reduction procedures are described particularly in European Patent Applications 0094792 and 0107995.

In the case of the compounds of formula (II), the intermediate (III) is initially converted into an intermediate (IV), where appropriate through an intermediate (V) when E has a chain length more than 1 carbon atom.

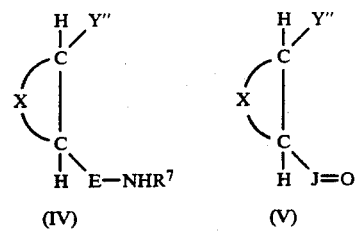

in which E and $R^7$ are as defined previously, Y" is as defined previously for Y' and J is a trivalent unsubstituted or substituted or aliphatic hydrocarbon group with a chain length of at least 2 carbon atoms which corresponds to the divalent group E but with the replacement by a free valency of a hydrogen atom attached to that carbon atom of the group E which is nitrogen-bonded, this carbon atom together with the oxo group forming a carbonyl group at the end of the group J=O [when E is a methylene group or a methylene group substituted by an araliphatic group then (IV) will be directly preparable from (III); when E is a methylene group substituted by an aromatic group, an intermediate (III) may be used in which $R^2$ is an aromatic group and the other groups are as previously defined, such a compound (III) being prepared from the formyl analogue by a Grignard reaction followed by oxidation of the product.] The procedures for preparing the compounds (V) and (IV) from the compounds (III) are directly analogous to those described in UK Patent 2113678, the preference among the compounds (IV) and (V) as regards the groups E—$NHR^7$ and J=O being as expressed therein for the groups A—$NHR^2$ and B=O respectively.

It will be appreciated that the compounds (IV) and (V) are novel and that such compounds are included within the scope of the present invention. Moreover, when the compounds (IV) contain a group $R^7$ which is other than hydrogen they are also of interest for use as biologically active compounds in the same way as the compounds (II). It is preferred that compounds (IV) for such a use contain a group E which is a substituted or particularly an unsubstituted methylene group. The compounds (IV) are of interest for use as biologically active compounds when $R^7$ is an aromatic group, a substituted aliphatic hydrocarbon group, particularly one which is directly substituted and especially an unsubstituted aliphatic hydrocarbon group. Preferences among such groups $R^7$ are generally as indicated hereinbefore for the compounds (II) but for unsubstituted aliphatic hydrocarbon groups $R^7$ the preference is for $C_{5-12}$ groups, for example straight and branched chain groups of 5, 6, 7 or 8 carbon atoms.

Pharmaceutical compositions containing compounds (I), (II), and (IV) according to the present invention are of interest in various contexts for their inhibition of thromboxane activity, which is believed to be caused by a thromboxane antagonism, uses of the compounds including the treatment of thrombotic disorders and also the treatment of anaphylactic disease states, for example as bronchodilators for the treatment of asthma, in hypoxia, etc. They additionally have potential as anti-inflammatory agents. It will be appreciated that the spectrum of activity shown by any particular compound will vary and that certain compounds may be of particular interest in one of these pharmaceutical applications whilst other compounds are of particular interest in another of them. It is of interest that the exhibition of a prostacyclin-like activity by certain compounds, particularly those possessing a group R of the form OR³ wherein R³ is a diphenylmethyl or like group, tends to be less significant with the compounds of the present invention than it is with those containing a natural group R¹. Moreover, although preferred compounds show a pure antagonist activity in the rabbit aorta system, some other compounds may show a partial antagonist activity in this test although they are antagonists in the human platelet system. Any compounds showing such a partial enhancing action on the thromboxane activity are also of some interest in respect of this activity, although to a much lesser extent than with inhibitory activity. Thus, certain compounds according to the present invention may be of interest for laboratory or even for pharmaceutical purposes, for example in the control of bleeding by topical administration which avoids any systemic take-up, by virtue of the thromboxane enhancing facet of their activity which is shown under certain conditions.

Derivatisation of the terminal carboxy group of R¹ may be useful in imparting a particular property to a compound which is of value to its formulation. Thus, for example, esters and other carboxy group derivatives can have advantages in relation to slow release depot preparations through their conversion in vivo to the compound containing a free carboxy group, although the low water solubility of the esters must be taken account of. Alternatively, the use of a compound in which the carboxy group is in salt form, for example the sodium salt, can be of value due to the enhancement of water solubility which generally results.

The compounds may be formulated for use as pharmaceuticals for both animal and particularly human administration by a variety of methods, but usually together with a physiologically acceptable diluent or carrier. The compounds may, for instance, be applied as an aqueous or oily solution or as an emulsion for parenteral administration, the composition therefore preferably being sterile and pyrogen-free. The compounds may also be compounded for oral administration in the presence of conventional solid carrier materials such a starch, lactose, dextrin and magnesium sterate. Alternative formulations are as aerosols, suppositories, cachets, and, for localised treatment, as suitable creams or drops. Without commitment to a rigid definition of dosage, which is difficult in view of the different levels of activity, methods of formulation, and methods of administration, some general guidance may be given. In the case of systemic administration to produce a thromboxane antagonism the normal daily dosage which is proposed lies in the range from about 0.1 mg to about 10 mg per kilogram (the average weight of human being about 70 kg) and particularly from about 1 mg to about 5 mg per kilogram. It will be appreciated, however, that dosages outside this range may be considered, for example in the case of topical application to produce a localised thromboxane antagonism, and that the daily dosage may be divided into two or more portions.

The invention is illustrated by the following Examples.

In the Examples the stereochemistry which the compounds are believed to possess has been indicated, the amounts of 5-exo, 6-endo and 5-endo, 6-exo isomers present in the mixture of bicyclo [2,2,2] oct-2Z-ene trans isomers being thought to be approximately equal.

In all cases some contamination of a minor nature by isomers other than those specified may be present, for example with the bicyclo-heptane ring systems by the other of the pairs of preferred isomers illustrated hereinbefore for the ring system in question, or particularly by the corresponding cis isomer. It will be appreciated that the proportion of such contaminants does not necessarily depend upon the stereochemical nature of the intermediates in earlier stages of the synthesis. Thus, certain compounds are capable of epimerisation under particular conditions, and the formyl compounds (III) in particular can undergo an epimerisation involving the formyl group, for example at the stage in the synthesis of many of these compounds where the formyl group is generated by the action of acid on an acetal.

In most cases the compounds are obtained in the form of a racemic mixture but in the case of the compounds of Examples 12 and 13 an optically active starting material is used and these compounds are therefore also optically active. It should also be noted that the full stereochemistry has not been designated in the names of the compounds of Examples 12 and 13 in as far as no attempt has been made to indicate the orientation of the substituents at the 5- and 6-positions relative to the two bridging groups —CH₂— and —C(CH₃)₂—, the full orientation being as shown in the structure designated 2α, 3β, 6α, illustrated hereinbefore.

EXAMPLES

EXAMPLE 1

5-endo-(6'-Ethoxycarbonyl-5'-oxahexyl)-6-exo-acetyl-bicyclo [2,2,2] oct-2Z-ene and
5-exo-(6'-ethoxycarbonyl-5'-oxahexyl)-6-endo-acetyl-bicyclo [2,2,2] oct-2Z-ene (1) Ethyl 8-hydroxy-3-oxa-octanoate A solution of 1,5-pentanediol (50 g, 480 mmol) in 100 ml of dry, redistilled dimethylformamide (DMF), is added dropwise, under nitrogen, to sodium hydride (11.3 g, 480 mmol) in 300 ml DMF (obtained from 19.2 g of a 60% w/v dispersion of sodium hydride in oil by washing with sodium dried petroleum spirit). After the addition is complete (about 45 minutes) the reaction mixture is heated to about 70° C. and stirring is continued for a further 4 hours when all hydrogen evolution has ceased. The reaction mixture is then cooled to 0° C. and ethyl bromoacetate (80.2 g; 480 mmol) is added, the ester being added in one portion in order to minimise ester cleavage by the basic reaction medium. After cessation of the consequent vigorous reaction, the mixture is heated at about 70° C. for a further 2 to 3 hours before the removal of the majority of the solvent by vacuum distillation. On cooling, the residue is poured into water and the product is isolated by ethyl acetate extraction and purified by chromatography on Florisil to provide the title compound as an oil (61.2 g, 67%), $\nu_{max}$ (film): 3450, 1740, 1195, 1130 cm⁻¹.

A good purification of this product is not easy to achieve in view of the contamination by the compound HO—(CH₂)₅OCOCH₂Br. In a variation of this procedure the mixed products from the reaction with the ethylbromoacetate may each be converted via their tetrahydropyranyl ethers to the title compound by the procedure described and illustrated in the main text.

(2) Ethyl 7-formyl-3-oxaheptanoate

To a solution of dimethylsulphoxide (18.6 ml, 263 mmol) in 75 ml of $CH_2Cl_2$ at $-60°$ C. under nitrogen, is added dropwise a solution of trifluoroacetic anhydride (27.8 ml, 197 mmol) in 75 ml of $CH_2Cl_2$, over about 15 minutes. The reaction mixture is stirred for a further 15 minutes at $-60°$ C. and the hydroxy/ester (1) (25 g, 132 mmol) in 150 ml $CH_2Cl_2$ is then added at such a rate as to keep the reaction temperature below $-60°$ C. (over about 30 minutes). After a further 15 minutes at this temperature, triethylamine (55 ml, 395 mmol) is added slowly over about 15 minutes, the reaction mixture is allowed to warm to ambient temperature (about 1.5 hours) and is then quenched with water. The product is isolated by extraction with dichloromethane and purified by chromatography on Florisil to provide the title compound as an oil (20.7 g, 84%), $\nu_{max}$ (film) 1750, 1725, 1195, 1130 $cm^{-1}$.

(3) Ethyl 10-oxo-8(E)-oxa-undecenoate

A solution of dimethyl 2-oxopropyl-phosphonate (10.6 g, 64 mmol) in 50 ml of dry, redistilled tetrahydrofuran (THF) is added over a period of about 20 minutes to a vigorously stirred suspension of sodium hydride (1.5 g, 64 mmol) in THF (obtained from 2.5 g of a 60% w/v dispersion of sodium hydride in oil by washing with sodium dried petroleum spirit), under nitrogen. The resulting suspension of a flocculant precipitate is stirred for a further 1 hour and the aldehyde/ester (2) (10 g, 53 mmol) in 50 ml THF is then added dropwise. The reaction mixture is stirred for a further 3 to 4 hours at room temperature before quenching with a 1% v/v aqueous solution of acetic acid. The product is isolated by ether extraction and purified by chromatography on silicic acid, the desired fraction being eluted in toluene/ethyl acetate (90:10 v/v), to provide the title compound as an oil (7.5 g, 62%), $\nu_{max}$ (film) 1745, 1670, 1620, 1190, 1125 $cm^{-1}$; $\lambda_{max}$ (MeOH) 222 nm, $\epsilon_{max}$ 3488.

(4)
5-endo-(6'-Ethoxycarbonyl-5'-oxahexyl)-6-exo-acetyl-bicyclo [2,2,2] oct-2Z-ene and 5-exo-(6'-ethoxycarbonyl-5'-oxahexyl)-6-endo-acetyl-bicyclo [2,2,2] oct-2Z-ene To a solution of the enone/ester (3) (2.5 g, 11 mmol) in 50 ml of sodium dried benzene is added a catalytic amount of boron trifluoride etherate (0.27 ml; 2.2 mmol), followed by cyclohexa-1,3-diene (2.1 ml; 22 mmol). The resulting solution is refluxed under nitrogen for 4 to 5 hours and, on cooling, the mixture is poured onto a saturated aqueous solution of sodium hydrogen carbonate. The product is isolated by ether extraction and purified by chromatography on Florisil, the desired fraction being eluted in toluene/ethyl acetate (95:5 v/v), to yield the mixture of title compounds as an oil (1.9 g, 56%), $\nu_{max}$ (film) 1750, 1705, 1195, 1130, 700 $cm^{-1}$; $\delta(CDCl_3)$ 6.35 (1H, dd), 6.00 (1H, dd), 4.16 (2H, q), 4.00 (2H, s), 3.51 (2H, t), 2.75 (1H, m), 2.4 (1H, m), 2.08 (3H, s), 1.92–1.05 (12H, m), 1.28 (3H, t).

EXAMPLE 2 trans-5-(6'-Carboxy-5'-oxahexyl)-6-acetyl-bicyclo [2,2,2] octane

(1)
trans-5-(6'-Ethoxycarbonyl-5'-oxahexyl)-6-acetyl-bicyclo [2,2,2] octane The mixture of 5-endo-(6'-ethoxycarbonyl-5'-oxahexyl)-6-exoacetyl-bicyclo [2,2,2] oct-2Z-ene and 5-exo-(6'-ethoxycarbonyl-5'-oxahexyl)-6-endo-acetyl-bicyclo [2,2,2] oct-2Z-ene (2.0 g, 65 mmol, prepared as in Example 1), is dissolved in ethanol and a catalytic amount of palladium on activated charcoal (10% w/w) is added. The resulting mixture is vigorously stirred under an atmosphere of hydrogen until the uptake of hydrogen is complete. The catalyst is removed by filtration through a Celite plug and the filtrate evaporated to give, as an oil, the title compound in admixture with trans-5-(4'-hydroxy)-6-acetyl-bicyclo [2,2,2] octane in a ratio of 55:45 w/w ester:alcohol[1].

[1] Better catalytic selectivity in favour of the ester is achieved by the use of Wilkinson's catalyst or ruthenium on carbon.

(2) trans-5-(6'-Carboxy-5'-oxahexyl)-6-acetyl-bicyclo [2,2,2] octane

The mixture from (1) is dissolved in dioxan/water (1:1 v/v) and an aqueous solution of 2M NaOH is added to give a final base concentration of N/20. The reaction mixture is heated for 2.5 hours at about 60° C. then cooled and poured into water. The aqueous phase is washed with ether to remove the alcohol component of the starting material and is then acidified to pH 3–4 and the desired product isolated by ether extraction. The extract is purified by chromatography on silicic acid, the desired fraction being eluted in toluene/ethyl acetate (85:15 v/v), to yield the title compound as an oil (1.9, 56%), $\nu_{max}$ (film) 1750, 1705, 1195, 1130, 700 $cm^{-1}$; $\delta(CDCl_3)$ 6.35 (1H, dd), 6.00 (1H, dd), 4.16 (2H, q), 4.00 (2H, s), 3.51 (2H, t), 2.75 (1H, m), 2.4 (1H, m), 2.08 (3H, s), 1.92–1.05 (12H, m), 1.28 (3H, t).

EXAMPLE 3 trans-5-(6'-Carboxy-5'-oxahexyl)-6-[1'-(O-diphenylmethoxyimino)ethyl]-bicyclo [2,2,2] octane trans-5-(6'-Carboxy-5'-oxahexyl)-6-acetyl-bicyclo [2,2,2] octane (100 mg, 0.35 mmol, prepared as described in Example 2) in 2 ml dioxan is added to diphenylmethylhydroxylamine hydrochloride (170 mg, 0.7 mmol) in 20 ml of anhydrous pyridine and the mixture is heated for 3 hours at 60° C. The majority of the solvent is then removed and the remaining solution is partitioned between ether and water at pH 3–4. The ether layer is dried and evaporated and the resulting residue purified by liquid-gel partition chromatography using Partisil (10) ODS with acetonitrile/water (70:30 v/v) containing 1% v/v glacial acetic acid run at 3 ml/minute (elution time 12.4 minutes) to give the title compound as a colourless oil (113.7 mg, 69%), $\lambda_{max}$ ($CH_3OH$) 258 nm, $\epsilon_{max}$ 545.2; $\delta(CDCl_3)$ 9.88 (1H, s), 7.28 (10H, m), 6.19 (1H, s), 4.00 (2H, s), 3.38 (2H, t), 1.87 (3H, s), 1.69–0.95 (18H, m).

EXAMPLE 4 trans-5-(6'-Carboxy-5'-oxahexyl)-6-(1'-[N-(phenylthiocarbamoyl)-hydrazono]-ethyl)-bicyclo [2,2,2] octane trans-5-(6'-Carboxy-5'-oxahexyl)-6-acetyl-bicyclo [2,2,2] octane (100 mg, 0.35 mmol, prepared as described in Example 2) in 2 ml dioxan is added to 4-phenylthiosemicarbazide (120 mg, 0.7 mmol) in 20 ml dioxan and the resulting solution is heated for 3 hours at 60° C. The solvent is then removed in vacuo and the residue is purified by liquid-gel partition chromatography using Partisil (10) ODS with acetonitrile/water (70:30 v/v) containing 1% v/v glacial acetic acid run at 3 ml/minute (elution time 15.1 minutes) to give the title compound as a yellow oil (137 mg, 90%), $\lambda_{max}$ (CH$_3$OH) 278 nm, $\epsilon_{max}$ 21120; $\delta$(CDCl$_3$) 9.42 (1H, br), 9.34 (1H, br) 8.99 (1H, br), 7.74–7.15 (5H, m), 4.00 (2H, s) 3.48 (2H, t), 1.95 (3H, s), 1.86–1.15 (18H, m).

EXAMPLE 5 trans-5-(6'-Carboxy-5'-oxahexyl)-6-(7'-[N-(p-methoxyphenyl-carbamoyl)-hydrazono]-ethyl)-bicyclo [2,2,2] octane trans-5-(6'-Carboxy-5'-oxahexyl)-6-acetyl-bicyclo [2,2,2] octane (0.1 g, 0.35 mmol—prepared as described in Example 2) and 4-p-methoxyphenylsemicarbazide (0.13 g, 0.7 mmol) in dioxan are heated for 2 hours at 50° C. The solvent is then removed in vacuo and the residue purified by liquid-gel partition chromatography as described in Example 3 to give an oil which is crystallised from a 20 mg/ml solution in ethanol at $-20°$ C. to give the title compound as white crystals, (95 mg, 60%), m.p. 143° C., $\lambda_{max}$ 249.5 nm, $\epsilon_{max}$ 19600; $\epsilon$(CDCl$_3$) 11.3 (1H, broad), 9.5 (1H, broad), 8.16 (1H, broad), 7.36 (2H, m), 6.85 (2H, m), 3.99 (2H, s), 3.75 (3H, s), 3.48 (2H, t), 1.89 (3H, s), 2.4–1.15 (18H, m).

EXAMPLE 6 trans-5-(6'-Carboxy-5'-oxahexyl)-6'-(1'-[N-(hexylthiocarbamoyl)-hydrazono]-ethyl)-bicyclo [2,2,2] octane trans-5-(6'-Carboxy-5'-oxahexyl)-6-acetyl-bicyclo [2,2,2] octane is reacted with 4-n-hexylsemicarbazide in an analogous manner to that described in Example 5 for 4-p-methoxyphenylsemicarbazide. The reaction mixture is again worked up in an analogous manner to give the title compound as an oil in about 50% yield, $\delta$(CDCl$_3$) 8.8 (2H, broad), 7.55 (1H, broad), 4.07 (2H, s), 3.62 (4H, m), 1.90 (3H, s), 2.3–0.8 (29H, m).

EXAMPLE 7 trans-5-(7'-Carboxy-6'-oxaheptyl)-6-acetyl-bicyclo [2,2,2] octane

The procedure of Examples 1 and 2 is followed but commencing with 1,6-hexanediol instead of 1,5-pentanediol to give ethyl 9-hydroxy-3-oxanonanoate. This compound is then converted through a similar series of reactions to those described in Examples 1 and 2 as follows, the amount of material and yield of product being indicated in brackets (the other reactants specified in Examples 1 and 2 are used in the same molar proportion as in those examples with solvents being used in the same proportion of volume of solvent:weight of reactant).

| Reactant | Product |
|---|---|
| Ethyl 9-hydroxy-3-oxanonanoate (4 g) | Ethyl 8-formyl-3-oxaoctanoate (3.0 g, 77%) |
| Ethyl 8-formyl-3-oxaoctanoate (2.7 g) | Ethyl 11-oxo-9(E)-3-oxadodecanoate (2.2 g, 61%) |
| Ethyl 11-oxo-9(E)-3-oxadodecanoate (2.2 g) | 5-endo-(7'-Ethoxycarbonyl-6'-oxaheptyl)-6-exo-acetyl bicyclo[2,2,2] oct-2Z-ene and 5-exo-(7'-ethoxycarbonyl-6'-oxaheptyl)-6-endo-acetyl-bicyclo[2,2,2] oct-2Z-ene (1.8 g, 62%) |
| 5-endo-(7'-Ethoxycarbonyl-6'-oxaheptyl)-6-exo-acetyl bicyclo[2,2,2] oct-2Z-ene and 5-exo-(7'-ethoxycarbonyl-6'-oxaheptyl)-6-endo-acetyl-bicyclo[2,2,2] oct-2Z-ene (1.8 g) | trans-5-(7'-Ethoxycarbonyl-6'-oxaheptyl)-6-acetyl bicyclo[2,2,2] octane (1.7 g, 94%) |
| trans-5-(7'-Ethoxycarbonyl-6'-oxaheptyl)-6-acetyl-bicyclo[2,2,2] octane (1.7 g) | trans-5-(7'-Carboxy-6'-oxaheptyl)-6-acetyl-bicyclo[2,2,2] octane (1.4 g, 90%) |

The last mentioned product, which is the title compound, is obtained as an oil, $v_{max}$ (film) 1730 (broad), 1705, 1125 cm$^{-1}$; $\delta$(CDCl$_3$) 9.55 (1H, br), 4.08 (2H, s), 3.52 (2H, t), 2.13 (3H, s), 2.15 (1H, m), 1.85 (1H, m), 1.75–1.1 (18H, m).

In a variation of this procedure the method used for the isolation of the product of the reaction of 1,6-hexane diol and ethyl bromoacetate may be varied as described in the variation of Example 1(2).

EXAMPLE 8 trans-5-(7'-Carboxy-6'-oxaheptyl)-6-(1'-[N-(phenylthiocarbamoyl)-hydrazano]-ethyl)-bicyclo [2,2,2] octane trans-5-(7'-Carboxy-5'-oxaheptyl)-6-acetyl-bicyclo [2,2,2] octane (100 mg, 0.34 mmol, prepared as described in Example 3) in 1 ml dioxan is added to 4-phenylthiosemicarbazide (113 mg; 68 mmol) in 20 ml dioxan and the resulting solution is heated for 3 hours at 60° C. The solvent is then removed in vacuo and the residue is purified by liquid-gel partition chromatography using Partisil (10) ODS with acetonitrile/water (70:30 v/v) containing 1% v/v glacial acetic acid run at 3 ml/minute (elution time 17.8 minutes), to give the title compound as a yellow oil (119.7 mg, 80%), $\lambda_{max}$ (CH$_3$OH) 287.5 nm, $\epsilon_{max}$ 25810; $\delta$(CDCl$_3$) 9.45 (2H, br), 8.96 (1H, br), 7.08–7.65 (5H, m), 4.00 (2H, s), 3.43 (2H, t), 1.96 (3H, s), 2.25–1.85 (2H, m), 1.8–1.1 (18H, m).

EXAMPLE 9

5-endo-(6'-Carboxy-2',5'-dioxahexyl)-6-exo-formyl-bicyclo [2,2,1]-heptane (A)

(1) 5-endo-Hydroxymethyl-6-exo-(1',3'-dioxacyclopent-2-yl)-bicyclo [2,2,1] heptane 5-endo-Ethoxycarbonyl-6-exo-diethoxymethyl-bicyclo [2,2,1] heptane is prepared as described in Example 1(4) of UK Patent 2039480 and then subjected to transacetalation by heating in toluene under a Dean and Stark head with an excess of ethylene glycol in the presence of a catalytic amount of p-toluene sulphonic acid. Removal of the solvent in vacuo yields 5-endo-ethoxycarbonyl-6-exo-(1',3'-dioxacyclopent-2'-yl)-bicyclo [2,2,1] heptane as an oil. To a stirred suspension of lithium aluminium hydride (0.7 g, 18.3 mmol) in sodium dried ether under nitrogen is added 5-endo-ethoxycarbonyl-6-exo-(1',3'-dioxacyclopent-2'-yl)-bicyclo [2,2,1] heptane (4 g, 16.7 mmol) at such a rate as to keep the ether refluxing gently. On completion of the addition the reaction mixture is refluxed for a further 90 minutes before cooling and carefully adding 50:50 v/v aqueous tetrahydrofuran to remove the excess reagent. The white granular precipitate is removed by filtration, the filtrate is dried over MgSO$_4$ and the solvent is removed in vacuo to give the title compound as an oil (2.97 g, 94%), $\nu_{max}$ (film) 3400, 2935, 2860, 1400, 1060, 1015 cm$^{-1}$.

(2)

5-endo-(3'-Ethoxycarbonyl-2-oxapropyl)-6-exo-(1',3'-dioxacyclopent-2'-yl)-bicyclo [2,2,1] heptane A solution of the alcohol/acetal (1) (2.5 g, 12.6 mmol) and ethyl diazoacetate (1.73 g, 15.2 mmol) in CH$_2$Cl$_2$ is cooled to 0°-5° C. and then treated with borom trifluoride etherate (155 μl, 1.26 mmol). The reaction mixture is allowed to come to room temperature over a period of 45 minutes when the production of nitrogen has ceased. The reaction mixture is then treated with an equal volume of saturated aqueous NaHCO$_3$ and stirred for a further 15 minutes. The layers are then separated and the aqueous phase washed with CH$_2$Cl$_2$. The combined organic layers are washed with brine and dried over MgSO$_4$, the solvent then being removed in vacuo to give the title compound in crude form. Purification is effected by chromatography on Florisil, the desired fraction being that eluted in 95:5 v/v toluene:ethyl acetate which provides the title compound as an oil (2.7 g, 75%), $\nu_{max}$ (film) 2935, 2855, 1750, 1195, 1125 cm$^{-1}$.

(3)

5-endo-(4'-Hydroxy-2'-oxabutyl)-6-exo-(1',3'-dioxacyclopent-2'-yl)-bicyclo [2,2,1] heptane The ester/acetal (2) (2.5 g, 8.8 mmol) in sodium dried ether is added dropwise to a stirred suspension of lithium aluminium hydride (0.38 g, 9.7 mmol) in sodium dried either under nitrogen at such a rate as to keep the ether refluxing gently. On completion of the addition the reaction mixture is refluxed for a further 60 minutes before cooling and quenching with 50:50 v/v aqueous tetrahydrofuran. The white precipitate is removed by filtration, the filtrate dried over MgSO$_4$ and the solvent removed in vacuo to give the title compound as an oil (1.9 g, 89%), $\nu_{max}$ (film) 3420, 2935, 2840, 1400, 1110, 1050 cm$^{-1}$.

(4)

5-endo-(6'-Carboxy-2',5'-dioxahexyl)-6-exo-(1',3'-dioxacyclopent-2'-yl)-bicyclo [2,2,1] heptane A solution of the alcohol/acetal (3) (1.75 g, 7.2 mmol) and ethyl diazoacetate (1.0 g, 8.7 mmol) in CH$_2$Cl$_2$ is cooled to 0°-5° C. and then treated with borom trifluoride etherate (90 μl, 0.72 mmol). The reaction mixture is allowed to come to room temperature over 45 minutes whilst nitrogen is produced. A saturated aqueous solution of NaHCO$_3$ is then added and the mixture vigorously stirred for a further 15 minutes. The layers are separated and the aqueous phase washed with CH$_2$Cl$_2$. The combined organic phases are washed with brine, dried over MgSO$_4$ and the solvent removed in vacuo to give 5-endo-(6'-ethoxycarbonyl-2',5'-dioxahexyl)-6-exo-(1',3'-dioxacyclopent-2'-yl)-bicyclo [2,2,1] heptane.

This ester/acetal is dissolved in dioxan (50 ml) to which water (45 ml) and aqueous 2N NaOH (5 ml) are added to provide a final concentration of 0.1N. The resulting solution is heated at about 60° C. for 2.5 hours, cooled and poured into water, the mixture being extracted with ether. The aqueous phase is carefully acidified to a pH of 2 to 3, the mixture extracted with ether, the ether extract dried over MgSO$_4$ and evaporated to give the title compound as an oil.

(5)

5-endo-(6'-Carboxy-2',5'-dioxahexyl)-6-exo-formyl-bicyclo [2,2,1] heptane

A solution of the acid/acetal (4) (1.1 g, 3.7 mmol) in CHCl$_3$ is vigorously stirred at room temperature with concentrated hydrochloric acid (10 ml) for 2.5 hours. The layers are separated and the aqueous phase is washed with CHCl$_3$. The combined organic phases are washed with H$_2$O, dried with MgSO$_4$ and the solvent removed to give the crude title compound. Purification is effected by chromatography on silicic acid, the fraction eluted in 20 to 50% v/v ethyl acetate in toluene being evaporated to provide 5-endo-(6'-carboxy-2',5'-dioxahexyl)-6-exo-formyl-bicyclo [2,2,1] heptane as an oil, $\nu_{max}$ (film) 3400-2500 (broad), 2940, 2860, 2750, 1750, 1715, 1110 cm$^{-1}$; δ(CDCl$_3$) 9.59 (1H, d), 9.35 (1H, broad), 4.13 (2H, s), 3.85-3.40 (6H, m), 2.60-2.10 (2H, m), 1.85 (1H, m), 1.75-1.10 (7H, m); M$^+$299.

(B)

In a variation of the procedure described under (A) the alcohol/acetal (3) is prepared in an alternative manner by tosylation of the alcohol/acetal (1), followed by treatment with sodium hydride and ethylene glycol in dimethylsulphoxide to give (3).

In a further variation of the procedure described under (A) the tosylated product described above, 5-endo-p-toluenesulphonyloxymethyl-6-exo-(1',3'-dioxacyclopent-2'-yl)-bicyclo [2,2,1] heptane is treated with sodium hydride and 3-oxapentane 1,5-diol in dimethyl sulphoxide to give 5-endo-(7'-hydroxy-2',5'-dioxaheptyl)-6-exo-(1',3'-dioxacyclopent-2'-yl)-bicyclo [2,2,1] heptane. This alcohol/acetal is then oxidised using pyridinium dichromate to give the acid/acetal (4) by this different route.

EXAMPLE 10

5-endo-(6'-Carboxy-2',5'-dioxahexyl-6-exo-(o-diphenylmethoxyiminomethyl)-bicyclo [2,2,1] heptane 5-endo-(6'-Carboxy-2',5'-dioxahexyl-6-exo-formyl-bicyclo [2,2,1] heptane (0.1 g, 0.39 mmol; prepared as described in Example 9) is heated in pyridine (20 ml) with diphenylmethyl hydroxylamine hydrochloride (0.184 g, 0.78 mmol) at about 50° C. for 3 hours. The bulk of the solvent is the removed in vacuo and the residue partitioned between either and water at pH 3. The aqueous phase is washed with ether and the combined organic phases are washed with brine, dried over MgSO$_4$ and the solvent removed in vacuo. The residue is purified by liquid gel partition chromatography using Partisil (10) ODS with acetonitrile/water (70:30 v/v) containing 1% v/v glacial acetic acid to give the title compound as an oil (122 mg, 72%), $\lambda_{max}$ (CH$_3$OH) 245 nm, $\epsilon_{max}$ 1431; δ(CDCl$_3$) 9.5 (1H, broad), 7.29 (10H, m), 7.42 and 6.5H (1H, d), 6.18 (1H, s), 4.06 (2H, s), 3.55 (6H, m), 2.4-1.9 (3H, m), 1.85-1.05 (7H, m).

EXAMPLE 11

5-endo-(6'-Carboxy-2',5'-dioxahexyl-6-exo-[N-(p-methoxyphenylcarbamoyl)-hydrazonomethyl]-bicyclo [2,2,1] heptane 5-endo-(6'-Carboxy-2',5'-dioxahexyl-6-exo-formyl-bicyclo [2,2,1] heptane (0.1 g, 0.39 mmol; prepared as described in Example 9) and 4-p-methoxyphenyl semicarbazide (141 mg, 0.78 mmol) in dioxan (20 ml) are heated at 50° C. for 3 hours. The solvent is then removed in vacuo and the residue purified by liquid-gel partition chromatography using Partisil (10) ODS with acetonitrile/water (70:30 v/v) containing 1% v/v glacial acetic acid to give the title compound as a pale yellow oil (115 mg, 71%), $\lambda_{max}$ (CH$_3$OH) 248.5 nm, $\epsilon_{max}$ 17600; $\delta$(CDCl$_3$) 10.13 (1H, broad), 9.75 (1H, broad), 7.93 (1H, broad), 7.38 (2H, m), 6.82 (2H, m), 7.19 and 6.38 (1H, dx2), 4.13 (2H, s), 3.75 (3H, s), 3.90–3.45 (6H, m), 2.4–1.1 (10, m).

EXAMPLE 12

2α-(7'-Carboxy-3',6'-dioxaheptyl)-3β-formyl-6,6-dimethyl-bicyclo [3,1,1] heptane (1)

2α-(4'-Ethoxycarbonyl-3'-oxabutyl)-3β-(1',3'-dioxacyclopent-2'-yl)-6,6-dimethyl-bicyclo [3,1,1] heptane 2α-(2'-Hydroxyethyl)-3β-(dimethoxymethyl)-6,6-dimethyl [3,1,1] heptane is prepared as described in Example 6(4) of UK Patent 2081258 and is then subjected to transacetalation by heating in toluene under a Dean and Stark head with an excess of ethylene glycol in the presence of a catalytic amount of p-toluene sulphonic acid. Removal of the solvent in vacuo gives 2α-(2'-hydroxyethyl)-3-(1',3'-dioxacyclopent-2'-yl)-6,6-dimethyl-bicyclo [3,1,1] heptane as an oil.

To a solution of this alcohol/acetal in dichloromethane at 0° C. is added ethyldiazoacetate (1.2 molar equivalents) followed by boron trifluoride etherate (0.1 molar equivalents) in ether. The reaction mixture is stirred and allowed to come to room temperature over 30 minutes whilst nitrogen is produced by the reaction. An equal volume of a saturated aqueous solution of NaHCO$_3$ is then added and the mixture is vigorously stirred for a further 15 minutes. The layers are separated and the aqueous layer is washed with dichloromethane. The combined organic phases are washed with brine, dried over MgSO$_4$ and the solvent removed in vacuo; the residue then being purified by chromatography on Florisil in 20% v/v ethyl acetate in toluene to give the title compound as an oil in 55% yield, $\delta$(CDCl$_3$) 4.78 (1H, s), 4.18 (2H, q), 4.0 (2H, s), 3.88 (4H, m), 3.52 (2H, t), 2.4–0.8 (aliphatic H, m), 1.28 (3H, s), 1.19 (3H, s), 1.0 (3H, s).

(2)

2α-(5'-Hydroxy-3'-oxapentyl)-3β-(1',3'-dioxacyclopent-2'-yl)-6,6-dimethyl-bicyclo [3,1,1] heptane The ester/acetal (1) in sodium dried ether is added dropwise to a stirred suspension of lithium aluminium hydride (1.1 molar equivalents) in sodium dried ether under nitrogen at such a rate as to keep the ether refluxing gently. On completion of the addition the reaction mixture is refluxed for a further 60 minutes before cooling and then quenching with 50:50 v/v aqueous tetrahydrofuran. The white precipitate is removed by filtration, the filtrate dried over MgSO$_4$ and the solvent removed in vacuo to give the title compound as an oil in 82% yield, $\delta$(CDCl$_3$) 4.8 (1H, s), 3.9 (4H, m), 3.65 (6H, m), 2.5–0.8 (aliphatic H, m), 1.19 (3H, s), 0.9 (3H, s).

(3)

2α-(7'-Ethoxycarbonyl-3',6'-dioxaheptyl)-3β-(1',3'-dioxacyclopent-2'-yl)-6,6-dimethyl-bicyclo [3,1,1] heptane A solution of the alcohol/acetal (2) and ethyl diazoacetate (1.2 molar equivalents) in dichloromethane is cooled to 0°–5° C. and then treated with boron trifluoride etherate (0.1 molar equivalents) in ether. The reaction mixture is allowed to come to room temperature over 30 minutes whilst nitrogen is produced by the reaction. An equal volume of a saturated aqueous solution of NaHCO$_3$ is then added and the mixture is vigorously stirred for a further 15 minutes. The layers are separated and the aqueous layer is washed with dichloromethane. The combined organic phases are washed with brine, dried over MgSO$_4$ and the solvent removed in vacuo; the residue then being purified by chromatography on Florisil in 50% v/v ethyl acetate in toluene to give the title compound as an oil in 56% yield, $\delta$(CDCl$_3$) 4.78 (1H, s), 4.2 (4H, m), 3.88 (4H, m), 3.55 (6H, m), 2.5–0.9 (aliphatic H), 1.29 (3H, s), 1.18 (3H, s), 0.99 (3H, s).

(4)

2α-(7'-Carboxy-3',6'-dioxaheptyl)-3β-formyl-6,6-dimethyl-bicyclo [3,1,1] heptane The ester/acetal (3) is dissolved in dioxan to which an equal volume of 0.2N aqueous KOH is added to provide a final concentration of 0.1N. The resulting solution is then heated at 50° C. for 3 hours, cooled and poured into water. The mixture is extracted with ether and the aqueous phase is then carefully acidified to a pH of 2 to 3 and re-extracted with ether. This ether extract is dried over MgSO$_4$ and evaporated to give 2α-(7'-carboxy-3',6'-dioxaheptyl)-3β-(1',3'-dioxacyclopent-2'-yl)-6,6-dimethyl-bicyclo [3,1,1] heptane as an oil.

This acid/acetal in a 6N hydrochloric acid/chloroform mixture is vigorously stirred for 2 hours at room temperature. The layers are separated and the aqueous phase is washed with CHCl$_3$. The combined organic phases are washed with water, dried over MgSO$_4$ and the solvent removed. Chromatography of the residue on silicic acid in 10% v/v ethyl acetate in toluene gives the title compound in an overall yield of 53%, $\delta$(CDCl$_3$) 9.6 (1H, s), 8.9 (1H, broad), 4.15 (2H, s), 3.6 (6H, m), 2.4–0.8 (aliphatic H, m), 1.2 (3H, s), 1.0 (3H, s), M+ (methyl ester-butyloxime) 383.

EXAMPLE 13

2α-(7'-Carboxy-3',6'-dioxaheptyl)-3β-[N-(phenylcarbamoyl)-hydrazonomethyl]-6,6-dimethyl-bicyclo [3,1,1] heptane 2α-(7'-Carboxy-3',6'-dioxaheptyl)-3β-formyl-6,6dimethyl-bicyclo [3,1,1] heptane (prepared as described in Example 12) and 4-phenylsemicarbazide (2 molar equivalents) in dioxan are heated at 50° C. for 3 hours. The solvent is then removed in vacuo and the residue purified by liquid-gel partition chromatography on 25% Lipidex using as eluant a mixture (by volume) of 100 parts of hexane, 100 parts of 1,2-dichloroethane and 2 parts of ethanol together with 0.1% v/v of the total of glacial acetic acid. Successive fractions with a volume of 4 ml are collected, the title compound being obtained as an oil from fractions 15 to 20 in 45% yield, $\delta$(CDCl$_3$) 9.85 (1H, broad), 8.58 (1H, broad), 8.1 (1H, broad), 7.65–6.9 (6H, m), 4.15 (2H, s), 3.55 (6H, m), 2.8–0.8 (aliphatic H), 1.22 (3H, s), 1.05 (3H, s); mass spectrum by direct inlet gives major ions at 373 (M-58), 212 (M-58-161) and 119 (M-312).

EXAMPLE 14

In Vitro Tests of Biological Activity

(1) Human Platelet System

Washed platelets are prepared by centrifugation of plateletrich human plasma at 600×g for 20 minutes. The platelet pellet is resuspended in $Ca^{++}$-free Kreb's solution.

Addition of the agonist 11.9-(epoxymethano) $PGH_2$ ($1 \times 10^{-7}$ to $5 \times 10^{-7}M$) causes immediate aggregation recorded as an increase in light transmission (600 nm). In a second experiment the compound under test is added 5 minutes previous to the addition of the $PGH_2$ analogue. The dose of the $PGH_2$ analogue added is then increased to a level which gives a similar response to that obtained in the absence of antagonist.

(2) Rabbit Aorta System

Spiral strips of thoracic aorta are suspended in Kreb's Henseleit solution and aerated with 95% $O_2$/5% $CO_2$ at 37° C. Tension changes are recorded with a Grass FT03 force transducer. Initially, cumulative dose response curves to 11,9-(epoxymethanol) $PGH_2$ ($2 \times 10^{-9}$, $1 \times 10^{-8}$, $5 \times 10$ and $2.5 \times 10^{-7}M$) are obtained. In a second experiment the individual compounds are added 30 minutes previous to the addition of the series of agonist doses.

(3) Guinea Pig Trachea System

Spiral strips of trachea are suspended in Kreb's-Henseleit solution, additionally containing atropine sulphate ($2 \times 10^{-8}M$) and indomethacin ($10^{-6}M$), aerated with 95% $O_2$/5% $CO_2$ and maintained at 37° C. Tension changes are recorded with a Grass FT03 force transducer. Initially, cumulative dose response curves to the agonist 11,9-(epoxymethano) $PGH_2$ are obtained (typically at the same concentrations as for the rabbit aorta system). In a second experiment, the compound under test is added 50 minutes previous to the addition of the series of agonist doses.

In the case of each system, the affinity constant, $K_B$, for the compound under test is calculated according to the Gaddum-Schild equation (based on Law of Mass Action).

$$DR-1 = [B] \times K_B \quad DR = \text{dose ratio}$$
$$[B] = \text{molar concentration of compound.}$$

In the human platelet system the compound trans-5-(6'-carboxy-5'-oxahexyl)-6-(1'-[N-(phenylthicarbamoyl)-hydrazono]-ethyl-bicyclo [2,2,2] octane typically gives a $K_B$ value of $2.1 \times 10^8$ ($M^{-1}$). By way of comparison the compound 5-endo-(6'-carboxyhex-2'-Z-enyl)-6-exo-(1'-[N-(phenylthiocarbamoyl)-hydrazono]-ethyl-bicyclo [2,2,1] heptane used as a control in the same experiment typically gives a $K_B$ value of $7 \times 10^7$ ($M^{-1}$).

The compound trans-5-(6'-carboxy-5'-oxahexyl)-6-[1'-(O-diphenylmethoxyimino)-ethyl]-bicyclo [2,2,2] octane when tested in the human platelet system showed very little prostacyclin-like activity as evidenced by antagonism of ADP.

Various compounds of formula (I) prepared in the previous Examples were tested in the rabbit aorta and guinea pig trachea systems, the results obtained being shown in the Table (in all of the compounds V and V' together are the second bond of a carbon-nitrogen double bond).

TABLE

| Compound | | | | $K_B \times 10^{-6}$ ($M^{-1}$) | |
|---|---|---|---|---|---|
| (bicyclo[2.2.2]octane) $R^1$ | $R^2$ | R | | Rabbit aorta | Guinea pig trachea |
| 6-carboxy-5-oxahexyl | $CH_3$ | $NHCSNHC_6H_5$ | | 6.0 | — |
| 6-carboxy-5-oxahexyl | $CH_3$ | p-$OCH_3$ substituted $NHCONHC_6H_5$ | | — | about 4,000 |
| 6-carboxy-5-oxahexyl | $CH_3$ | $NHCSNHC_6H_{13}$ | | — | 70 |
| 7-carboxy-6-oxaheptyl | $CH_3$ | $NHCSNHC_6H_5$ | | 5.2 | 270 |
| (bicyclo[2.2.1]heptane) 6-carboxy-2,5-dioxahexyl | H | $OCH(C_6H_5)_2$ | | 3.4 | 56 |

EXAMPLE 15

In Vivo Tests of Biological Activity

A male albino guinea pig is anaethetised with a mixture of allyl barbituric acid and ethyl carbamate and the guinea pig is given intravenously a dose of 0.35 μg/kg of 11,9-(epoxymethane) $PGH_2$. After a further period of 10 minutes, the guinea pig is treated intravenously with a dose of 0.3 mg/kg of trans-5-(6'-carboxy-5'-oxahexyl)-6-(1'-[N-phenylthiocarbamoyl-hydrazono]-ethyl-bicyclo [2,2,2] octane.

The guinea pig is then used in a modified Konzett-Rossler test which gives a measure of the inhibition produced by the test compound of the bronchoconstiction resulting from administration of the $PGH_2$ derivative. This test involves artificially respiring the animals and measuring the amount of residual air with a pressure transducer.

It was found that at the 0.3 mg/kg dose level the bicyclo [2,2,2] octane compound markedly blocked the action of the PGH$_2$ analogue whilst, when used in a control experiment at the same dose level without prior administration of the PGH$_2$ analogue, the bicyclo [2,2,2] octane compound did not itself lead to any observable bronchoconstriction.

We claim:

1. A compound of formula (I)

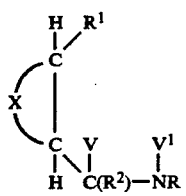

where

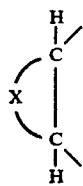

represents one of the divalent cyclic groups

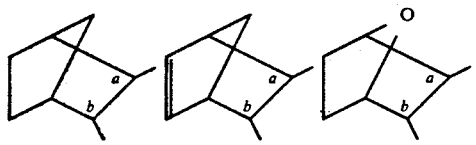

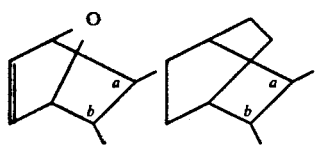

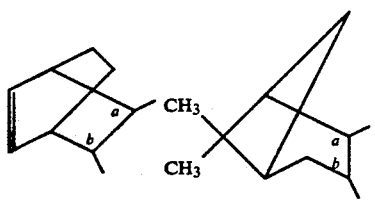

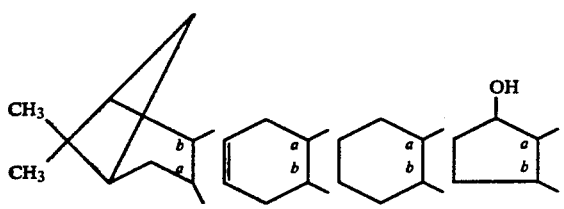

the letters a and b indicating in each case the points of attachment of the substituents R$^1$ and CV(R$^2$)—NV'R, respectively; R$^1$ is a group —(CH$_2$)$_c$—B—CH$_2$—CO$_2$R' in which B is oxygen or sulphur, c is an integer from 3 to 10 and CO$_2$R' is carboxy group or a physiologically acceptable amide, ester or salt derivative thereof; V and V' either each separately is hydrogen or together are the second bond of a carbon-nitrogen double bond; R$^2$ is hydrogen, a C$_{1-12}$ aliphatic hydrocarbon group or a C$_{1-12}$ aliphatic hydrocarbon group substituted by a group Ar, OAr or SAr, where Ar represents a phenyl, naphthyl, fluorenyl, dibenzocyclohexyl, dibenzocycloheptyl, pyridyl, benzthiazolyl, dihydrobenzthiazolyl, N-methyldihydro-benzthiazolyl, benzoxazolyl, dihydrobenzoxazolyl or N-methyldihydrobenzoxazolyl group or such a group substituted by one or more substituents selected from C$_{1-12}$ alkoxy, halogeno, C$_{1-12}$ halogeno-substituted alkyl, sulphamoyl, amino, hydroxyl, nitro and C$_{1-12}$ alkyl groups; and R is a group —D—R$^3$, —N=R$^5$ or —NW.G.W' in which D is —NH—, —NH.CS—, —NH.CO—, —NH.CO.CH$_2$N(R$^6$)—, —NH.SO$_2$—, —NH.CO.NH—, —NH.CS.NH—, —NH.CO.O— or —NH.CS.O—, G is —CO— or —CS— and W and W' together are a group —(CH$_2$)$_d$— in which d is 3, 4 or 5, R$^3$ is a C$_{1-12}$ aliphatic hydrocarbon group, a group Ar or a C$_{1-12}$ aliphatic hydrocarbon group substituted by one or more groups selected from Ar, OAr and SAr, R$^5$ is a C$_{1-12}$ aliphatic hydrocarbon group, a group Ar', where Ar' represents a fluorenylidene, dibenzocyclohexylidene, dibenzocycloheptylidene, dihydrobenzthiazolylidene, N-methyldihydrobenzthiazolylidene, dihydrobenzoxazolylidene or N-methyl- dihydrobenzoxazolylidene group or such a group substituted on a benzene ring or rings thereof by one or more substituents selected from C$_{1-12}$ alkoxy, halogeno, C$_{1-12}$ halogeno-substituted alkyl, sulphamoyl, amino, hydroxyl, nitro and C$_{1-12}$ alkyl groups, or a C$_{1-12}$ aliphatic hydrocarbon group substituted by one or more groups selected from Ar, OAr and SAr, and R$^6$ is hydrogen, a C$_{1-12}$ aliphatic hydrocarbon group, a group Ar or a C$_{1-12}$ aliphatic hydrocarbon group substituted by one or more groups selected from Ar, OAr and SAr.

2. A compound according to claim 1, in which the divalent cyclic group comprises a bicyclo [2,2,1] heptane, bicyclo [2,21] hept-2Z-ene, bicyclo [2,2,2] octane or bicyclo [2,2,2] oct-2Z-ene ring system.

3. A compound according to claim 1, in which R$^1$ is a group —(CH$_2$)$_c$—B—CH$_2$—CO$_2$R' wherein c is 4, 5 or 6.

4. A compound according to claim 1, in which B is oxygen.

5. A compound according to claim 1, in which R$^1$ is —(CH$_2$)$_4$—O—CH$_2$—CO$_2$H, —(CH$_2$)$_5$—O—CH$_2$CO$_2$H, or —(CH$_2$)$_6$—O—CH$_2$—CO$_2$H, or a salt derivative thereof.

6. A compound according to claim 1, in which the group CV(R$^2$)—NV'R is of the form C(R$^2$)=NR.

7. A compound according to claim 1, in which R$^2$ is hydrogen or an alkyl group of 1 to 3 carbon atoms.

8. A compound according to claim 1, in which R is a group —NH.CO.NHR$^3$ or —NH.CS.NHR$^3$.

9. A compound according to claim 1, which contains a group R$^3$ that is an alkyl group of 1 to 12 carbon atoms.

10. A compound according to claim 1, which contains a group R$^3$ that is a group Ar or an alkyl group of 1 to 3 carbon atoms substituted by one or more groups selected from Ar, OAr and SAr.

11. A compound according to claim 1, in which any Ar of OAr or SAr group is selected from unsubstituted phenyl and pyridyl groups.

12. A compound according to claim 1, in which the group CV(R²)—NV'R is of the form C(R²)=N—NH.CS.NHR³ wherein R² is hydrogen or methyl and R³ is an alkyl group of 5 to 10 carbon atoms, an unsubstituted phenyl group, or a methylene group directly linked to an unsubstituted or substituted phenyl group.

13. A compound according to claim 1, which contains a bicyclo [2,2,2] octane ring system having a substituent R¹ which is a group —(CH₂)ₑ—B—CH₂—CO₂R' wherein B is oxygen and c is 4, 5 or 6, and CO₂R' is a carboxy group or a salt derivative thereof, and a substituent CV(R²)—NV'R which is a group C(CH₃)=N—NH.CS.NNHR³ wherein R³ is an unsubstituted or substituted phenyl group.

14. A compound according to claim 11, in which the substituted phenyl groups have one or more substituents selected from C₁₋₃ alkoxy, halogeno, and C₁₋₁₂ halogeno-substituted alkyl, hydroxyl, nitro and sulphamoyl groups.

15. A compound according to claim 11, in which the substituent groups are selected from methyl, methoxy, dimethylamino, fluoro, chloro, bromo and trifluoromethyl.

16. A compound according to claim 1, in which the substituents R¹ and CV(R²)—NV'R are in a trans relationship.

17. A compound according to claim 16, in which the divalent cyclic group has the 5-endo, 6-exo configuration when it is a bicyclo [2,2,1] heptane, bicyclo [2,2,1] hept-2Z-ene or bicyclo [2,2,2] oct-2Z-ene, the 5-endo, 6-exo or 5-exo, 6-endo configuration when it is a 7-oxa-bicyclo [2,2,1] heptane or 7-oxa bicyclo [2,2,1] hept-2Z-ene, the 2α, 3β, 6α configuration when it is a 6,6-dimethyl-bicyclo [3,3,1] heptane and the 1α, 2α, 3β configuration when it is a 1-hydroxycyclopentane.

18. A compound according to claim 1, which contains a 5-endo, 6-exo-substituted bicyclo [2,2,1] heptane or a trans-5,6-substituted bicyclo [2,2,2] octane ring system wherein the substituent at the 5-position is a 7-carboxy-6-oxaheptyl or 6-carboxy-5-oxahexyl group or an amide, ester or salt derivative thereof and the substituent at the 6-position is a grouping C(R²)=NR in which R² is hydrogen, methyl or ethyl and R is —NHCSNH—C₆H₅ or —NHCONH—C₆H₅.

19. A compound according to claim 1, being 5-endo-(6'-carboxy-5'-oxahexyl)-6-exo-(1'-[N-(phenylthiocarbamoyl)-hydrazono]-ethyl)-bicyclo [2,2,1] heptane, 5-endo-(7'-carboxy-6-oxaheptyl)-6-exo-(1'-[N-(phenylthiocarbamoyl)-hydrazono]-ethyl)-bicyclo [2,2,1] heptane, trans-5-(6'-carboxy-5'-oxahexyl)-6-(1'-[N-(phenylthiocarbamoyl)-hydrazono]-ethyl)-bicyclo [2,2,2]octane or trans-5-(7'-carboxy-6'-oxaheptyl)-6-(1'-[N-(phenylthiocarbamoyl)-hydrazono]-ethyl)-bicyclo [2,2,2] octane, or a carboxylate salt thereof.

20. A compound of formula

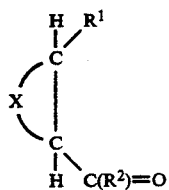

where

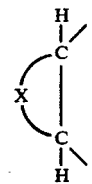

represents one of the divalent cyclic groups

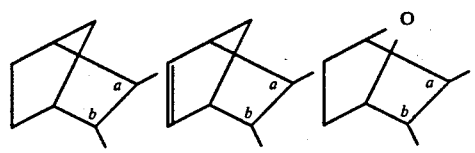

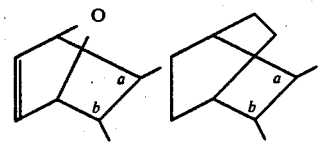

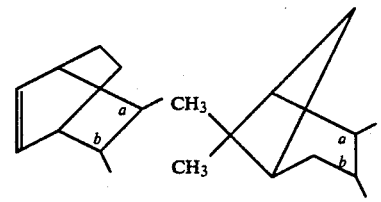

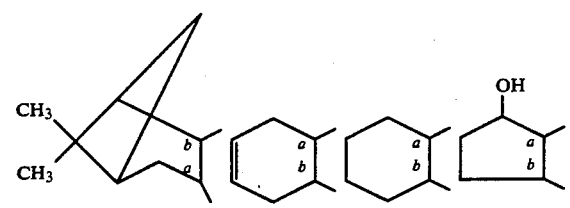

the letters a and b indicating that in each case the points of attachment of the substituents R¹ and C(R²)=O, respectively; R¹ is a group —(CH₂)ₑ—B—CH₂—CO₂R' in which B is oxygen or sulphur, c is an integer from 3 to 10 and CO₂R' is a carboxy group or a physiologically acceptable amide, ester or salt derivative thereof; R² is, a C₁₋₁₂ aliphatic hydrocarbon group or a C₁₋₁₂ aliphatic hydrocarbon group substituted by a group Ar, OAr or SAr, where Ar represents a phenyl, naphthyl, fluorenyl, dibenzocyclohexyl, dibenzocycloheptyl, pyridyl, benzthiazolyl, dihydrobenzthiazolyl, N-methyldihydrobenzthiazolyl, benzoxazolyl, dihydrobenzoxaolyl or N-methyldihydrobenzoxazolyl group or such a group substituted by one or more substituents selected from C₁₋₁₂ alkoxy, halogeno, C₁₋₁₂ halogeno-substituted alkyl, sulphamoyl, amino, hydroxyl, nitro and C₁₋₁₂ alkyl groups.

21. A compound according to claim 20, in which the divalent cyclic group comprises a bicyclo [2,2,1] heptane, bicyclo [2,2,1] hept-2-ene, bicyclo [2,2,2] octane or bicyclo [2,2,2] oct-2Z-ene ring system.

22. A compound according to claim 20, in which R¹ is a group —(CH₂)ₑ—B—CH₂—CO₂R' wherein c is 4, 5 or 6.

23. A compound according to claim 20, in which B is oxygen.

24. A compound according to claim 20, in which $R^1$ is $-(CH_2)_4-O-CH_2CO_2H$, $-(CH_2)_5-O-CH_2-CO_2H$, or $-(CH_2)_6-O-CH_2-CO_2H$, or a salt derivate thereof.

25. A compound according to claim 20, in which $R^2$ is an alkyl group of 1 to 3 carbon atoms.

26. A compound according to claim 25, in which $R^2$ is methyl.

27. A compound according to claim 21, which contains a bicyclo [2,2,2] octane ring system having a substituent $R^1$ which is a group $-(CH_2)_c-B-CH_2-CO_2R'$ wherein B is oxygen and $CO_2R'$ is a carboxy group or an ester derivative thereof, and a substituent $C(R^2)=O$ where $R^2$ is methyl or ethyl.

28. A compound according to claim 20, in which the substituents $R^1$ and $C(R^2)=O$ are in a trans relationship.

29. A compound according to claim 28, in which the divalent cyclic group has the 5-endo, 6-exo configuration when it is a bicyclo [2,2,1] heptane, bicyclo [2,2,1] hept-2Z-ene or bicyclo [2,2,2] oct-2Z-ene, the 5-endo, 6-exo or 5-exo, 6-endo configuration when it is a 7-oxabicyclo [2,2,1] heptane or 7-oxa-bicyclo [2,2,1] hept-2Z-ene, the $2\alpha$, $3\beta$, $6\alpha$ configuration when it is a 6,6-dimethyl-bicyclo [3,3,1] heptane and the $1\alpha$, $2\alpha$, $3\beta$ configuration when it is a 1-hydroxycyclopentane.

30. A compound according to claim 20 which contains a 5-endo, 6-exo-substituted bicyclo [2,2,1] heptane or a trans-5,6-substituted bicyclo [2,2,2] octane ring system wherein the substituent at the 5-position is a 7-carboxy-6-oxaheptyl or 6-carboxy-5-oxahexyl group or an amide, ester or salt derivative thereof and the substituent at the 6-position is a grouping $C(R^2)=O$ in which $R^2$ is methyl or ethyl.

31. A compound according to claim 20, being 5-endo-(6'-carboxy-5'-oxahexyl)-6-exo-acetyl-bicyclo [2,2,1] heptane, 5-endo-(7'-carboxy-6'-oxaheptyl)-6-exo-acetyl-bicyclo [2,2,1] heptane, trans-5-(6'-carboxy-5'-oxahexyl)-6-acetyl-bicyclo [2,2,2] octane, or an ester thereof.

32. A pharmaceutical composition for treating thrombotic disorders, anaphylactic disease states and conditions requiring anti-inflammatory treatment, said composition comprising a compound according to claim 1 as an active ingredient thereof, together with a physiologically acceptable diluent or carrier.

33. A method of treating thrombotic disorders, anaphylactic disease states and conditions requiring anti-inflammatory treatment in patients which comprises administering to the patient an amount of a compound according to claim 1 which is effective to inhibit thromboxane activity in the patient.

34. A compound according to claim 20, in which the group Ar of Ar, OAr or SAr has one or more $C_{1-3}$ alkoxy substituents.

35. A compound according to claim 34, in which the alkoxy substituents are methoxy.

36. A compound according to claim 12, in which $R^3$ is a substituted phenyl group in which the one or more substituents are selected from methyl, methoxy, dimethylamino, fluoro, chloro, bromo and trifuloromethyl.

37. A compound according to claim 36, in which the substituent group or groups are methoxy.

* * * * *

UNITED STATES PATENT AND TRADEMARK OFFICE
CERTIFICATE OF CORRECTION

PATENT NO. : 5,077,309

DATED : December 31, 1991

INVENTOR(S) : JONES et al

Page 1 of 3

It is certified that error appears in the above-identified patent and that said Letters Patent is hereby corrected as shown below:

First page of the patent, left hand column insert the following heading: Related U.S. application data --[62] continuation of Ser. No. 07/003,690, Jan 16, 1987, abandoned--

In the abstract in formula (I) delete "$V^1$" and replace by --V'--

Column 1 line 55 in formula (I) delete "$V^1$" and replace by --V'--

Column 3 line 60 delete the formula and replace by the following new formula:

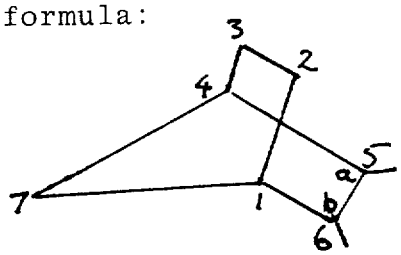

Column 35 line 18 in formula (I) delete "$V^1$" and replace by --V'--

UNITED STATES PATENT AND TRADEMARK OFFICE
CERTIFICATE OF CORRECTION

PATENT NO. : 5,077,309

DATED : December 31, 1991

INVENTOR(S) : JONES et al

Page 2 of 3

It is certified that error appears in the above-identified patent and that said Letters Patent is hereby corrected as shown below:

Column 36 line 1 insert --a-- before "carboxy"

Column 36 line 10 delete "N-methyldihydro-benzthiazolyl" and replace by --N-methyldihydrobenzthiazolyl--

Column 36 line 30 delete "N-methyl-dihydrobenzoxazolylidene" and replace by --N-methyldihydrobenzoxazolylidene--

Column 36 line 42 delete "[2,21]" and replace by --[2,2,1]--

Column 36 lines 50-51 delete and replace by the following:
$-(CH_2)_4-O-CH_2-CO_2H, -(CH_2)_5-O-CH_2-CO_2H$, or
$-(CH_2)_6-O-CH_2-CO_2H$, or a salt deriv- --

Column 37 lines 10-11 delete and replace by the following:
--stituent $R^1$ which is a group $-(CH_2)_c-B-CH_2-CO_2R'$ wherein B is oxygen and c is 4, 5 or 6, and--

Column 37 line 53 delete "[2,2,2]octane" and replace by --[2,2,2] octane--

UNITED STATES PATENT AND TRADEMARK OFFICE
CERTIFICATE OF CORRECTION

PATENT NO. : 5,077,309
DATED : December 31, 1991
INVENTOR(S) : JONES et al

It is certified that error appears in the above-identified patent and that said Letters Patent is hereby corrected as shown below:

Column 38 lines 46-47 delete and replace by the following:
--respectively; $R^1$ is a group $-(CH_2)_c-B-CH_2-CO_2R'$ in which B is oxygen or sulfur, c is an inte- --

Column 38 line 50 delete "," after "is"

Column 38 line 64 delete "hept-2-ene" and replace by --hept-2Z-ene--

Column 39 lines 4-5 delete and replace by the following:
--is $-(CH_2)_4-O-CH_2-CO_2H$, $-(CH_2)_5-O-CH_2-CO_2H$, or $-(CH_2)_6-O-CH_2-CO_2H$, or a salt--

Column 39 lines 13-14 delete and replace by the following:
--stituent $R^1$ which is a group $-(CH_2)_c-B-CH_2-CO_2R'$ wherein B is oxygen and $CO_2R'$ is a carboxy--

Signed and Sealed this

Thirteenth Day of July, 1993

Attest:

MICHAEL K. KIRK

Attesting Officer

Acting Commissioner of Patents and Trademarks